US012773554B2

(12) United States Patent
Smyth et al.

(10) Patent No.: US 12,773,554 B2
(45) Date of Patent: Oct. 27, 2026

(54) METHODS AND PHARMACEUTICAL FORMULATIONS FOR MODULATING THE PROPERTIES OF THE BLOOD LABYRINTH BARRIER

(71) Applicant: Cochlear Limited, Macquarie University (AU)

(72) Inventors: Daniel Smyth, Dublin (IE); Wolfram Frederik Dueck, Berlin (DE)

(73) Assignee: Cochlear Limited, Macquarie University (AU)

( * ) Notice: Subject to any disclaimer, the term of this patent is extended or adjusted under 35 U.S.C. 154(b) by 337 days.

(21) Appl. No.: 18/571,427

(22) PCT Filed: Jun. 23, 2022

(86) PCT No.: PCT/IB2022/055846
§ 371 (c)(1),
(2) Date: Dec. 18, 2023

(87) PCT Pub. No.: WO2022/269540
PCT Pub. Date: Dec. 29, 2022

(65) Prior Publication Data

US 2024/0278014 A1 Aug. 22, 2024

Related U.S. Application Data

(60) Provisional application No. 63/214,312, filed on Jun. 24, 2021.

(51) Int. Cl.
*A61N 1/36* (2006.01)

(52) U.S. Cl.
CPC ................................ *A61N 1/36038* (2017.08)

(58) Field of Classification Search
None
See application file for complete search history.

(56) References Cited

U.S. PATENT DOCUMENTS

| | | | | |
|---|---|---|---|---|
| 2001/0053872 A1* | 12/2001 | Zilberman | A61N 1/36038 600/25 |
| 2011/0295331 A1* | 12/2011 | Wells | A61N 5/0601 607/3 |
| 2020/0000879 A1 | 1/2020 | Wise et al. | |

(Continued)

FOREIGN PATENT DOCUMENTS

WO 2019180614 A1 9/2019

OTHER PUBLICATIONS

International Search Report and Written Opinion in counterpart International Application No. PCT/IB2022/055846, mailed Oct. 6, 2022, 8 pages.

(Continued)

*Primary Examiner* — Erica S Lee
(74) *Attorney, Agent, or Firm* — Edell, Shapiro & Finnan, LLC

(57) ABSTRACT

Methods and pharmaceutical formulations are provided for modulating permeability and other properties of the blood labyrinth barrier (BLB) of the inner car. Such methods could be used in known control systems for monitoring and treating CI recipients and individuals have hearing loss-related conditions, disorders and diseases, including for example. Meniere's disease.

20 Claims, 23 Drawing Sheets

(56) References Cited

U.S. PATENT DOCUMENTS

| | | | | |
|---|---|---|---|---|
| 2020/0248204 | A1 | 8/2020 | Smith et al. | |
| 2021/0001113 | A1* | 1/2021 | Smyth | A61B 5/12 |

OTHER PUBLICATIONS

Franco-Vidal, V. et al., "Zinc Protection against Pneumolysin Toxicity on Rat Cochlear Hair Cells," Audiology & Neurotology, 2008, vol. 13, 9 pages. https://doi.org/10.1159/000108763.

Kim, Kyu-Sung et al., "Effects of Caveolin-1 Expression and Epigallocatechin-3-gallate in Gentamicin-Exposed UB/UE-1 Cells," Journal of the Korean Balance Society, 2004, vol. 3, Issue 2, 2 pages.

Nyberg, S. et al., "Delivery of therapeutics to the inner ear: The challenge of the blood-labyrinth barrier," Sci. Transl. Med. vol. 11, Issue 482, Mar. 6, 2019, eaao0935 (2019), 12 pages. DOI:10.1126/scitranslmed.aao0935.

Salt, A. et al., "Time Course of Blood-Labyrinth Barrier Compromise Following Cochlear Implantation," Meeting of the Association for Research in Otolaryngology (ARO), Mar. 6, 2020, 1 page.

Connolly, T. et al., "Pre-operative intravenous dexamethasone prevents auditory threshold shift in a guinea pig model of cochlear implantation," Audiol Neurootol (2011) vol. 16, Issue 3, Jul. 29, 2010, 9 pages. DOI: 10.1159/000314757.

Le Floc'h, J. et al., "Markers of cochlear inflammation using MRI," Journal of Magnetic Resonance Imaging, Jan. 2014, vol. 39, Issue 1, 12 pages. DOI: 10.1002/jmri.24144.

* cited by examiner

METHODS AND PHARMACEUTICAL FORMULATIONS FOR MODULATING THE PROPERTIES OF THE BLOOD LABYRINTH BARRIER

BACKGROUND

Field of the Invention

Methods and pharmaceutical formulations are provided for modulating the permeability of the blood labyrinth barrier ("BLB") of the inner ear.

Related Art

Medical devices have provided a wide range of therapeutic benefits to recipients over recent decades. Medical devices can include internal or implantable components/devices, external or wearable components/devices, or combinations thereof (e.g., a device having an external component communicating with an implantable component). Medical devices, such as traditional hearing aids, partially or fully-implantable hearing prostheses (e.g., bone conduction devices, mechanical stimulators, cochlear implants (or "CI"), etc.), pacemakers, defibrillators, functional electrical stimulation devices, and other medical devices, have been successful in performing lifesaving and/or lifestyle enhancement functions and/or recipient monitoring for a number of years.

The types of medical devices and the ranges of functions performed thereby have increased over the years. For example, many medical devices, sometimes referred to as "implantable medical devices," now often include one or more instruments, apparatus, sensors, processors, controllers or other functional mechanical or electrical components that are permanently or temporarily implanted in a recipient. These functional devices are typically used to diagnose, prevent, monitor, treat, or manage a disease/injury or symptom thereof, or to investigate, replace or modify the anatomy or a physiological process. Many of these functional devices utilize power and/or data received from external devices that are part of, or operate in conjunction with, implantable components.

SUMMARY

Methods and pharmaceutical formulations are provided for modulating the properties of the BLB, specifically, for (1) attenuating or preventing increased permeability of the BLB seen in disease states such as Meniere's disease, or after physical or chemical-induced injury; (2) lowering or attenuating the immune response following implantation of a device; (3) lowering or attenuating the concentration or activity of caveolin-1 to reduce the production of transport vesicles; or (4) increasing permeability, increasing inflammatory responses or increased caveolin-1 activity for use in research settings.

In one embodiment is a method for modulating the permeability of the BLB comprising administering a pharmaceutical formulation of known concentration on a first side of the BLB; detecting the amount of the pharmaceutical formulation that has passed through the BLB using a biosensor positioned on the other side of said BLB.

In other embodiments disclosed we provide a method of modulating the BLB with a pharmaceutical formulation that comprises a combination of a corticosteroid and a vasoconstrictor, or a corticosteroid with either a compound with anti-caveolin-1 activity, or with a compound with anti-pneumolysin activity. In some embodiments the administration of the pharmaceutical formulation takes place systemically, while in other embodiments administration takes place locally, whether in the middle ear, in an artery supplying the middle and inner ear tissues, or through intracochlear means.

Embodiments disclosed for the various pharmaceutical formulations that may modulate the BLB properties such as permeability comprise the active compounds referenced above, as well as carriers, excipients and other non-active compounds that will vary in form (liquid, solid, gel, particle, etc.) depending on the formulation and the mode of administration (IV, IP, injection, delivery through cannula from deposit or refillable reservoir, enteral, topical, etc.), as well as whether a sustained release formulation is desired.

In still other embodiments a medical device such as a cochlear implant and/or a biosensor is employed to deliver the pharmaceutical formulation and/or to detect the concentration(s) of pharmaceutical formulations, etc. In some embodiments, the medical device comprises a component in a control system that, through an iterative process that may be fully automated, adjusts the administration of the formulation to modulate permeability of the BLB.

The embodiments disclosed for methods of modulating the BLB can be used prophylactically, to prevent, reduce or delay the progression of hearing loss or other auditory disorders associated with loss of BLB or other inner ear function. One embodiment discloses treating Meniere's and other patients having hearing loss with the disclosed methods and pharmaceutical formulations.

In some embodiments two or more pharmaceutical formulations may be administered simultaneously; in other embodiments two or more pharmaceutical formulations may be administered serially. Pharmaceutical carriers may be the same or different for each type (simultaneous, serial) of administration.

BRIEF DESCRIPTION OF THE DRAWINGS

Embodiments of the present invention are described herein in conjunction with the accompanying drawings, in which:

FIG. 8 shows plasma concentrations over time. The dotted line shows the calculated time course for injection. Perilymph sampling after IV injection began. The amount of dextran in perilymph was used as an index of blood labyrinth barrier permeability.

In FIG. 13, each sample time represents the mean of samples 1-6 from one ear; lines represent the group (n=5) mean. Early after implantation, entry of fluorescein, representing the permeability of the BLB, for both ears is similar, indicating that entry does not result from “insertion trauma.”

FIG. 16C depicts the location of the implant relative to the scala tympani (ST), and informs the data shown in FIG. 16B.

DETAILED DESCRIPTION

Figure 1A:
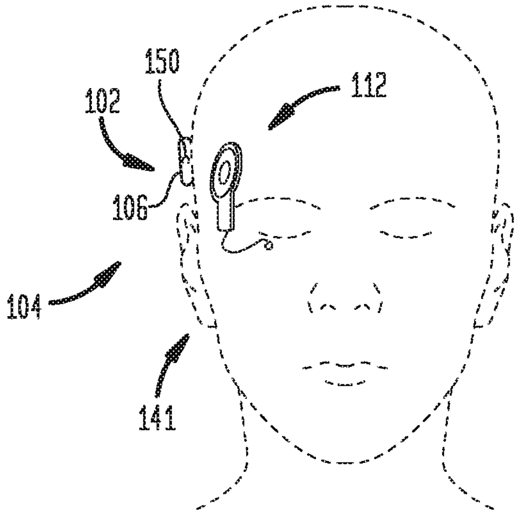
FIG. 1A is a schematic diagram illustrating a cochlear implant system with which certain embodiments presented herein may be implemented.

More than five percent of the global population has experienced some degree of hearing loss, which can result from damage to inner ear structures and loss of auditory neurons or cochlear sensory cells. The etiology of hearing loss is varied and includes exposure to loud noise, physical injury, advancing age, genetic factors as well as disorders and diseases (Wang et al., 2018; Nyberg et al., 2019; Blanc et al., 2020). One of the changes that has been noted to the structure and function of the inner ear in individuals with some degree of hearing loss is an increase in the permeability of the blood labyrinth barrier (Pakdaman et al., 2016; Ishiyama et al., 2017; Zhang et al., 2020).

The BLB functions much like the blood brain barrier (BBB) or the blood-cerebral spinal fluid barrier: permitting nutrients, hormones and water but preventing most other (large) molecules and compounds from leaving the blood and entering other fluid compartments and other tissues; at the same time, it transports wastes and toxins away from the tissues to the blood (Nyberg et al., *Sci. Transl. Med.* 11, eaao0935, 2019). In the case of the BBB and brain-cerebral spinal fluid barriers, the cerebral spinal fluid, extracellular fluid of the CNS and the brain are protected by the barriers; in the case of the BLB, perilymph and endolymph fluids and structures of the inner ear labyrinth are protected.

The permeability or integrity of the barriers including the BLB can be modulated by, among other things, drugs, irradiation, auditory trauma and physical disruption or injury and the resulting immune response, or non-invasive therapeutic treatments, such as focused ultrasound therapy (Sun et al. 2017). Inflammation, brought on by injury or irritation to the cells comprising the barrier or surrounding tissue, is a contributing factor in the loss of BLB integrity, making it more permeable to molecules and compounds that would otherwise not cross into the perilymph. Inflammatory cytokines, such as tumor necrosis factor-α (TNF-α), interleukin-1β (IL-1β) and interleukin-6 (IL-6) are some of the immune system molecules produced locally in response to injury or irritation; an infection is not required to elicit such a response (Wang et al., 2018).

In Meniere's disease, characterized by tinnitus, vertigo, and hearing loss, the structure of cells and tissues surrounding the capillaries is markedly changed from that of the non-diseased state (Ishiyama et al., 2017). While the tight junctions between endothelial cells comprising the walls of the capillaries and the BLB seem to remain intact (Id.), the increased permeability reported in Meniere's disease may relate at least in part to the significantly greater number of transport vesicles present in the vascular endothelial cells, the pericyte process detachment, and the disruption of the perivascular basement membrane surrounding the endothelial cells (Id.). In other conditions and in response to certain pharmaceutical agents, the tight junctions themselves may be compromised permitting larger molecules and compounds to pass to the tissues (Sawada et al., Tight junctions and human diseases. *Med Electron Microsc.;* 36(3): 147-56, 2003. doi: 10.1007/s00795-003-0219-y. PMID: 14505058).

To restore or improve hearing, implantable devices such as cochlear implants (CI) may be prescribed. The surgical implantation procedure, however, may lead to tissue damage ("insertion trauma") in the implantation area, resulting in an inflammatory response and possibly temporary hearing loss.

Inner ear implants including CI have been used for delivery of drugs to the inner ear, e.g., local delivery to the middle or inner ear into perilymph fluid through, for example, pumped from a refillable reservoir, or deposited as a gel in the middle ear for access through the round window, by cannula or by injection, or as a component of a coating on, or a delivery channel associated with, a CI electrode or other device component (Plontke et al., 2017; Wang et al., 2018). For example, glucocorticosteroids have been used to address inflammation and other issues in the auditory system following CI implantation and the "insertion trauma" at the BLB. Dexamethasone formulated in a polymer and coated on the electrodes of an implanted CI was shown to attenuate the loss of auditory sensory cells after exposure to tumor necrosis factor alpha (TNF-α); similarly, hearing loss induced by CI implantation could be reduced after administration of dexamethasone in a sustained release application (Plontke et al., 2017). Increased impedance and fibrosis associated with implant trauma, as well as the migration of immune cells into the cochlea, were reduced following administration of dexamethasone delivered through coated electrodes (Id.; Wang et al., 2018).

An implantable device has been described that monitors conditions inside the cochlea and treats a patient using a control system and human intervention to modulate properties and characteristics of the BLB, including attenuation of increased permeability of the BLB frequently seen in auditory disorders and diseases, with the goal of improving a patient's ability to hear (US 20210001113 A1).

Methods and pharmaceutical formulations are provided for modulating the properties of the blood labyrinth barrier (BLB) located at the interface between the blood supply and the inner ear labyrinth, which includes the perilymph and other inner ear tissues, including such methods and formulation that may be used in a system or process, or in combination with use of the devices disclosed in the above referenced US 20210001113 A1. Methods for evaluating the permeability of the BLB and modulating it are provided below.

Sensitive tissues in the body, e.g., the brain, ear and eye, are protected from circulating blood and its constituents by physiological barriers that prevent certain compounds, such as high molecular weight compounds, from diffusing from the blood into tissues and interstitial fluids. The blood brain barrier (BBB) in the brain separates blood from cerebral spinal and brain interstitial fluid. The blood retinal barrier (BRB) in the eyes separates blood from the retina, and in the inner ear the BLB separates blood from the perilymph and endolymph, and endolymph from other interstitial fluid. Certain diseases or disorders may lead to or result from, barrier dysfunction and leakage, for example, Meniere's disease, discussed further below. Although this disclosure focuses on monitoring, treating and preventing inflammation and the resulting increased permeability of the BLB, the embodiments disclosed herein may be used to monitor, treat and prevent conditions involving the BBB and the BRB, where deviations in the permeability of either of those barriers contributes to the disorder or disease.

Barriers such as the BLB are multicellular systems that respond to the local environment and regulate the environment of sensitive tissues while protecting the sensitive tissues or limiting exposure of the sensitive tissues to the circulatory system, which may contain toxins, bacteria, viruses or other components that may adversely impact the function of the sensitive tissues. Because these sensitive tissues are not self-regenerative, the barriers provide an extra layer of protection. The BLB comprises a distributed cellular network that lines the blood vessels, selectively supplying nutrients from the blood to the inner ear tissues and keeping most molecules and compounds in the blood separated from the tissues of the inner ear. At the same time, the BLB transports toxins and wastes out of the inner ear tissues into the blood.

In general, the BLB of the inner ear protects sensitive tissues by limiting the passage of most molecules from the blood into the perilymph and endolymph. Some immune cells are present within the cochlea, e.g., resident immune cells may include perivascular macrophages. The BLB may become more permeable in response to a variety of stimuli, including, e.g., cytokines and other chemical messengers released by these and other cells in response to injury or irritation. Cytokines, in some cases, in conjunction with other biological signals such as reduced connexin 26 expression, may recruit immune cells into the cochlea.

Cochlear implants may be surgically implanted into the cochlea to restore or improve hearing. Implantation may trigger an immune response by macrophages or other immune cells, recruiting additional immune cells (e.g., macrophages, NK cells, neutrophils, etc.) to the site of inflammation. In some cases, an elevated immune response may comprise the integrity of the BLB, i.e., it may lead to the BLB becoming more permeable to molecules and compounds it would otherwise not permit to pass to the inner ear tissues; the result may be some degree of hearing loss. Depending on the source of the damage or the condition, this permeability may be due to loss of integrity of the tight junctions between endothelial cells, and/or possibly through a marked increase in the vacuoles and transport vesicles observed in the cells of individuals with, e.g., Meniere's disease (Ishiyama et al., 2017). Regardless, in some cases, the immune response ultimately may lead to the destruction of sensitive cells and tissue governing hearing. In at least some situations, the degree of permeability is correlated with hearing loss. (Salt et al., 2020)

The loss of BLB integrity, i.e., degradation, is positively correlated with hearing loss (Salt et al., 2020). Inflammatory responses at or near the BLB are triggered by various stimuli including, e.g., implantation of a cochlear implant or other device that disrupts the BLB during implantation. The disclosed methods and pharmaceutical formulations, results in modulation of the immune response and, thus, improvement, restoration or protection of BLB integrity. In some embodiments, the immune response is restored to a pre-implantation level, or is restored within 5%, 10%, 15%, 20%, 25% of the preimplantation level). Alternatively, in some embodiments, pharmaceutical formulations may be administered at the time of implantation of a device to prevent inflammation from developing at the site, and the resultant damage and hearing loss. The methods described herein advantageously are used in conjunction with implantation of devices, such as cochlear implants, and may be used to maintain and/or restore the functioning of the BLB that may be disturbed by implantation of the device.

Anatomy of the Inner Ear

Figure 2:
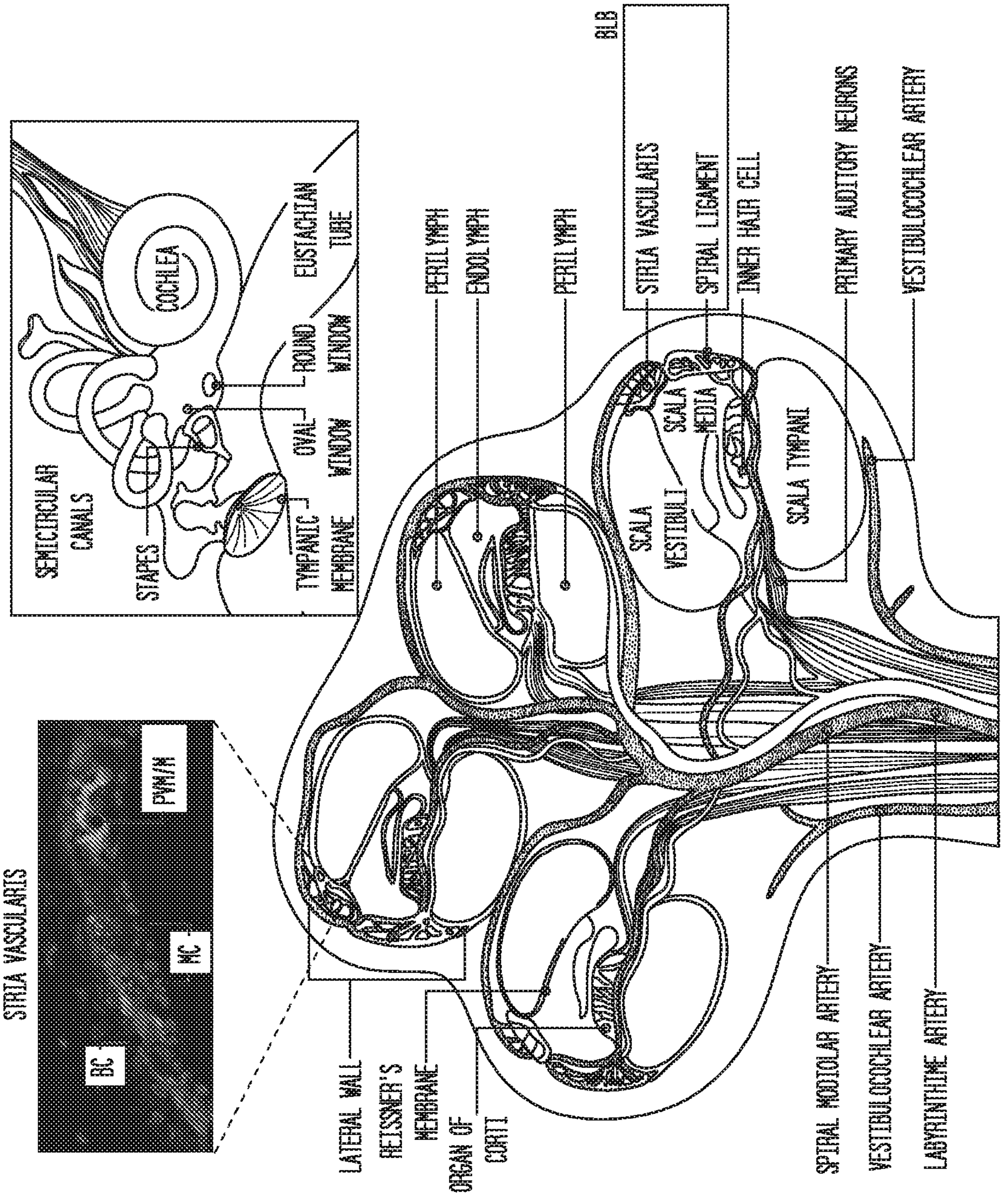
FIG. 2 is an illustration showing the location of the BLB.

FIG. 2 is an illustration of the arteries (dotted structure and identified as arteries) servicing the cochlea. The cells comprising the blood labyrinth barrier line regions comprising capillaries, such as the stria vascularis and spiral ligaments. Thus, the BLB acts a gate, allowing toxins and other molecules to travel to the capillaries, but preventing or reducing toxins and most other molecules from entering the cochlea from the bloodstream. The blood supplies nutrients to the cells of the BLB and other inner ear tissues.

The BLB complicates treatment of the inner ear, as it provides a formidable barrier the delivery of therapeutic substances by the circulatory system. While high doses of therapeutics may need to be administered systemically to elicit the desired effect in the inner ear, this also may cause deleterious side effects for the patient. The other treatment option for inner ear disorders and diseases is local administration of therapeutic substances.

Figure 3:
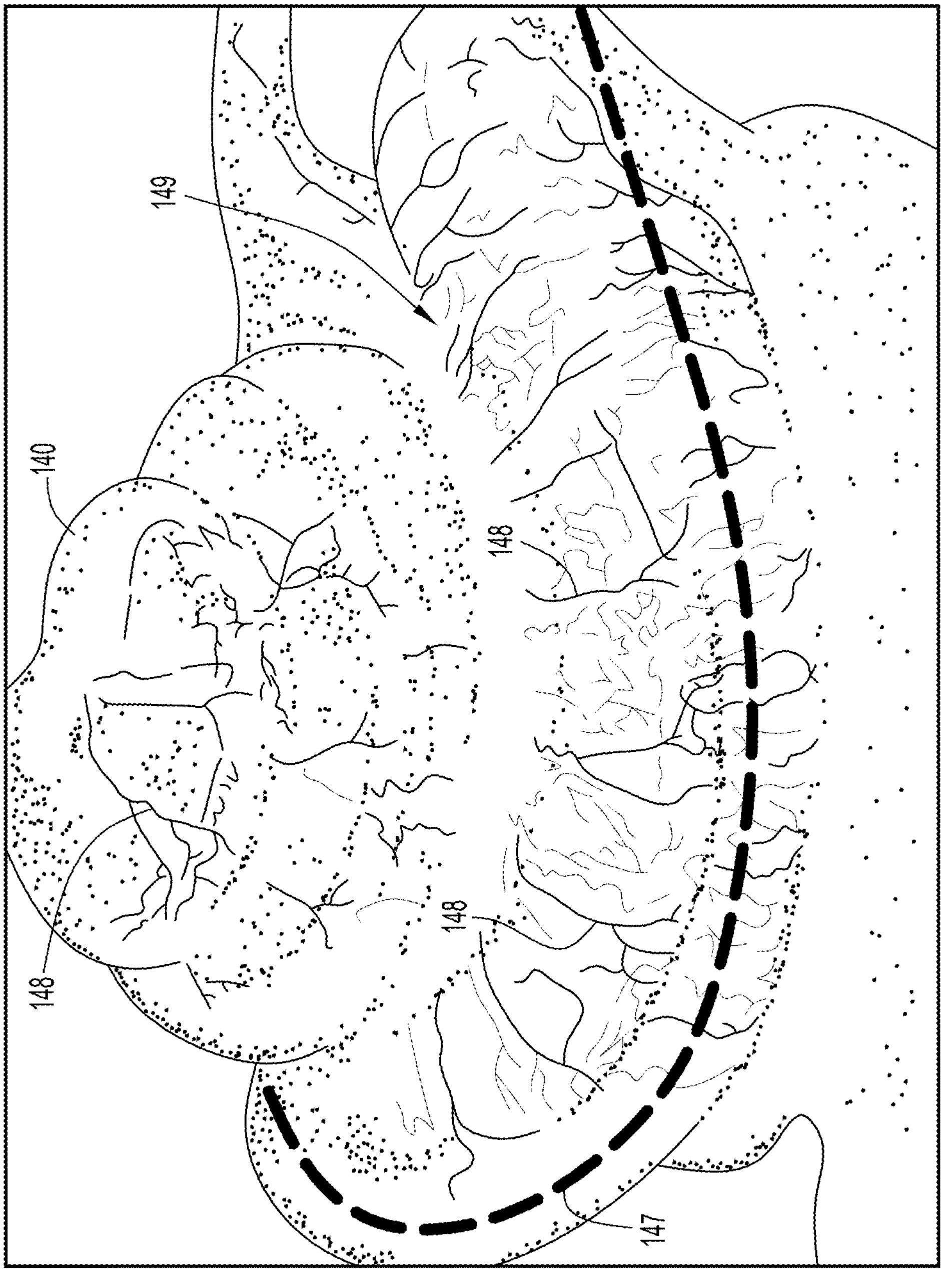
FIG. 3 is a photo illustrating a perspective of a human cochlea.
Figure 4:
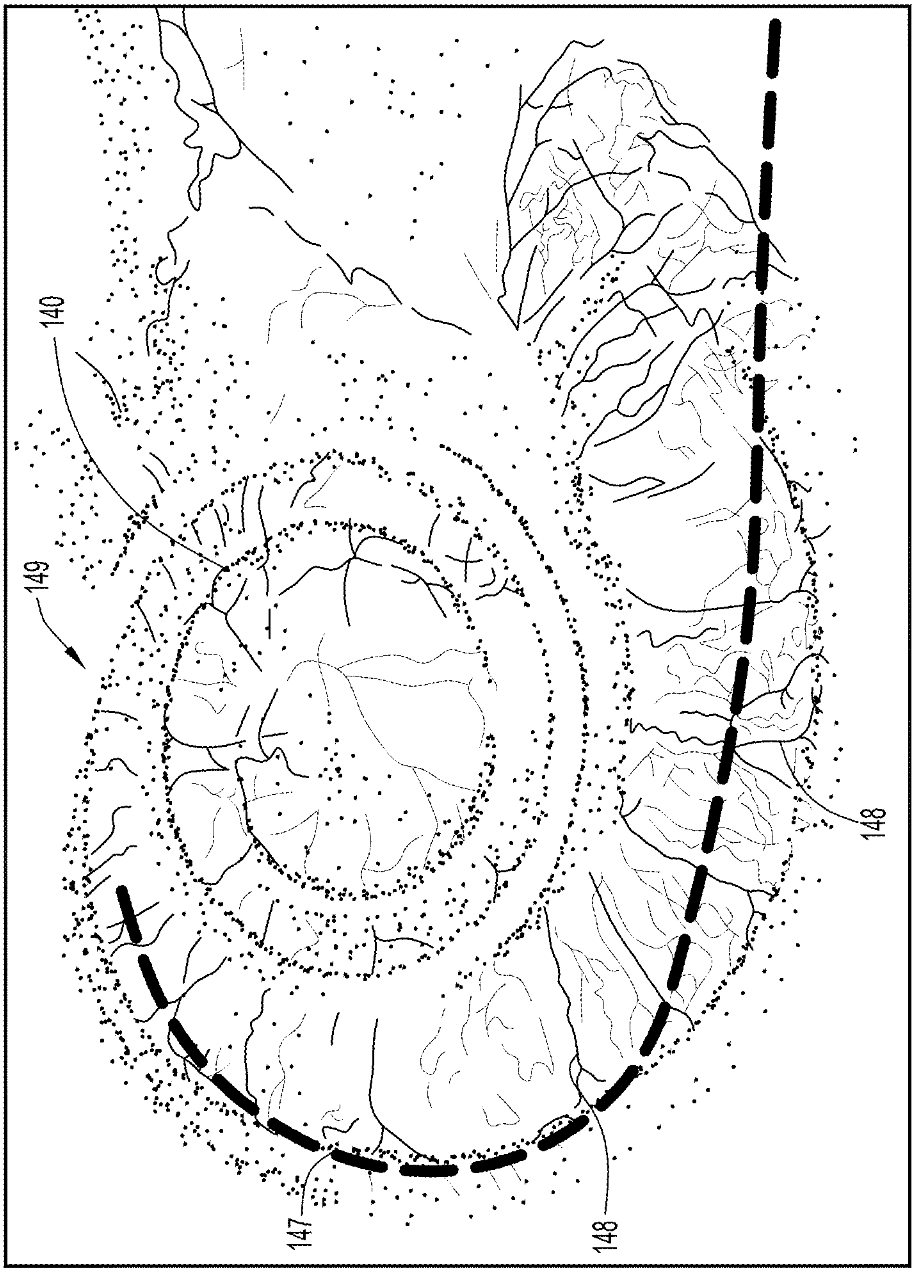
FIG. 4 is a photo illustrating a top view of the human cochlea of FIG. 3.

FIG. 3 is a photo illustrating a perspective of a cochlea 140, while FIG. 4 is a photo illustrating a top view of the cochlea 140. The photos of FIGS. 3 and 4 have been annotated to show the location/path 147 (hatched sections in sequence) of a stimulating assembly 118 within the cochlea 140.

FIGS. 3 and 4 also illustrate the outer wall 149 of the cochlea 140. As shown, there are numerous blood vessels 148 within the outer wall 149 of the cochlea 140. These blood vessels 148 provide a significant blood supply to the tissues of the cochlea 140, leaving oxygen and nutrients and transporting away wastes.

Figures 5A, 5B:
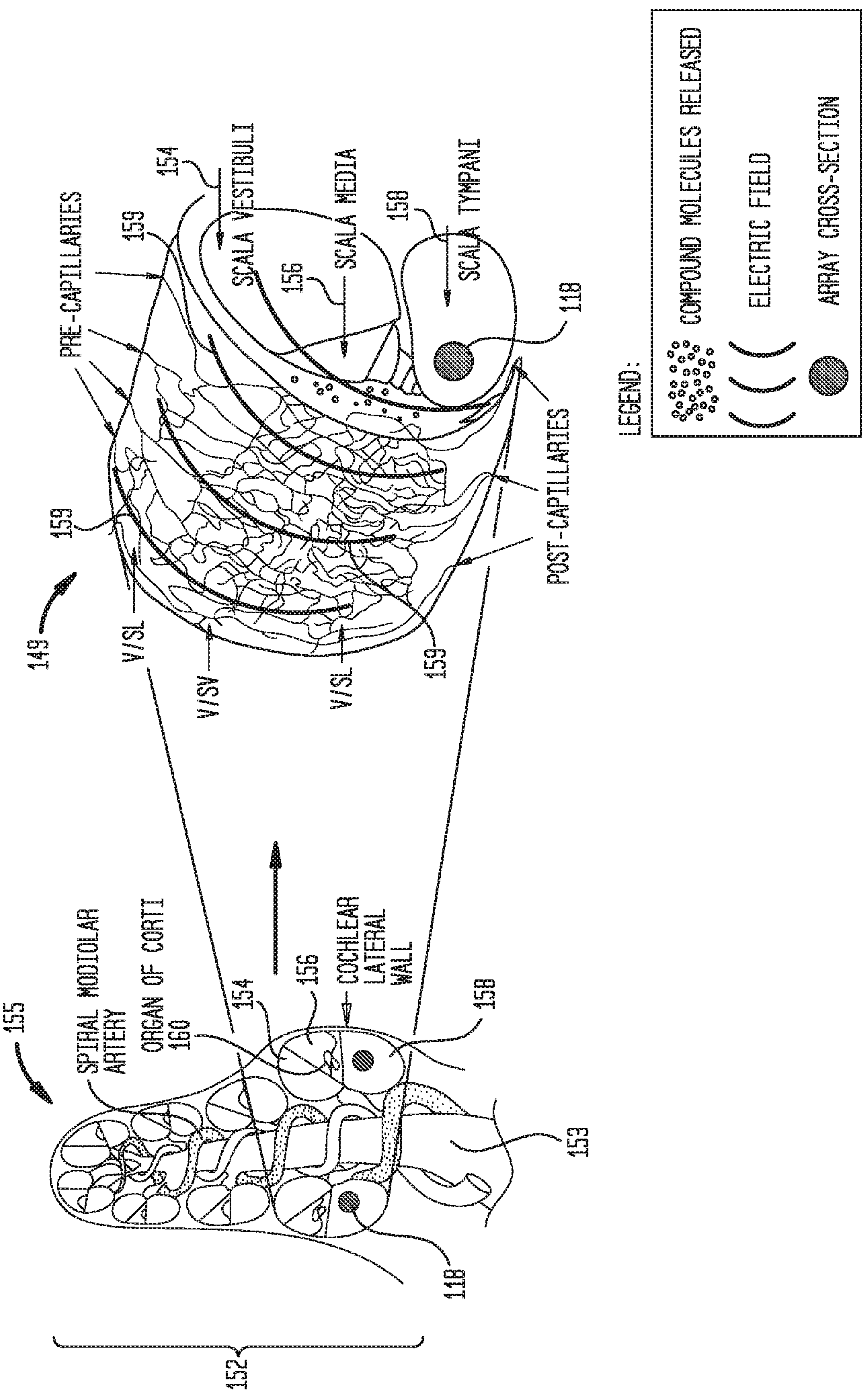
FIGS. 5A, 5B, and 5C are schematic diagrams illustrating further details of a human cochlea and the location/position of a stimulating assembly positioned therein, in accordance with certain embodiments presented herein.
Figure 5C:
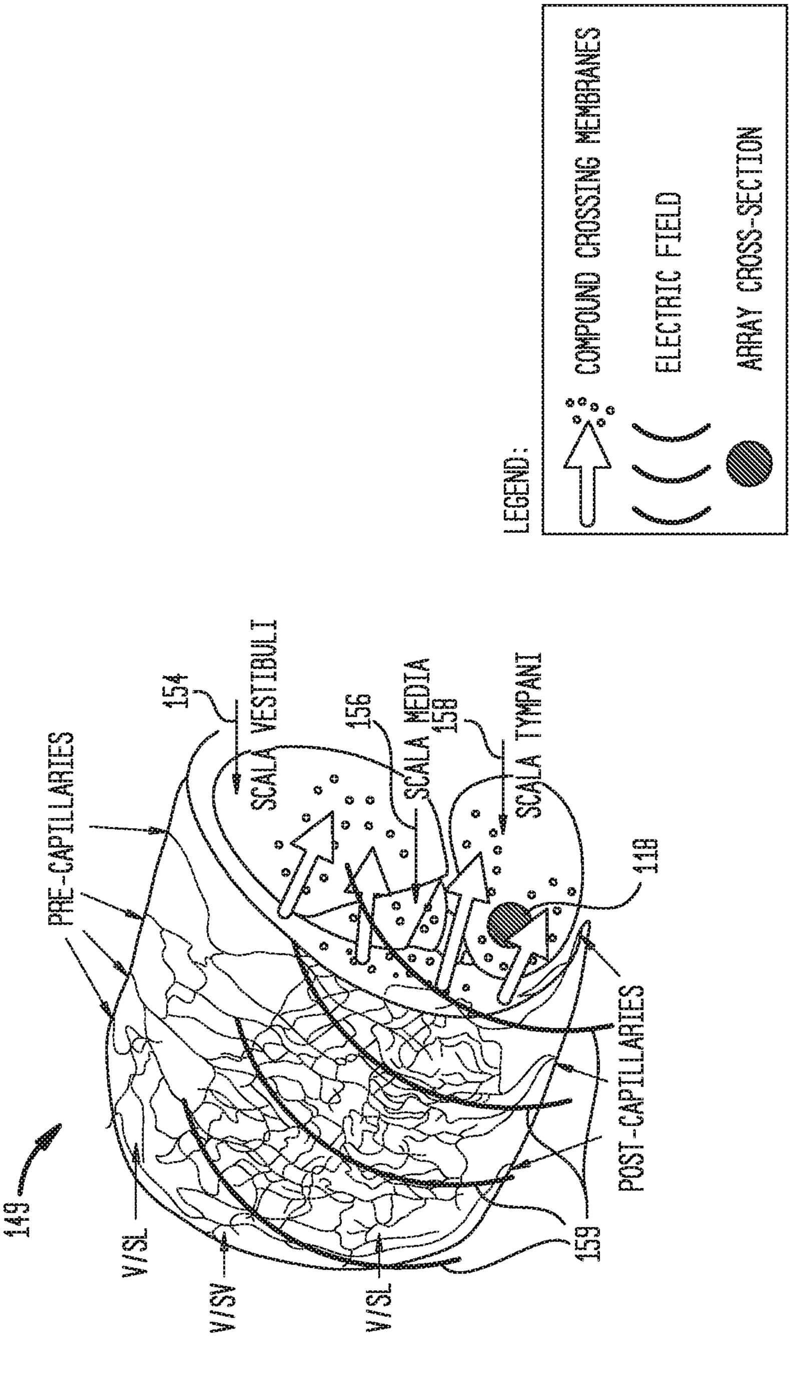

In addition, FIGS. 5A, 5B, and 5C are schematic diagrams illustrating further details of cochlea 140, as well as the location/position of stimulating assembly 118. More specifically, FIG. 5A is cross-sectional view of the cochlea 140 partially cut-away to display the canals of the cochlea 140, while FIGS. 5B and 5C are cross-sectional perspectives of one turn of the canals of the cochlea 140. FIGS. 5A-5C will be described together.

Cochlea 140 is a conical spiral structure comprising three parallel fluid-filled canals or ducts, collectively and generally referred to herein as canals 152. Canals 152 comprise the tympanic canal 158, also referred to as the scala tympani 158, the vestibular canal 154, also referred to as the scala vestibuli 154, and the median canal 156, also referred to as the scala media 156. Cochlea 140 spirals about modiolus 153 several times and terminates at cochlea apex 155. The organ of Corti 160 is situated on the basilar membrane in the scala media 156 and contains rows of 16,000-20,000 hair cells (not shown) which protrude from its surface. The stimulating assembly 118 (hatched cross-section circles) of cochlear implant 100 spirals around the modiolus 153 within the scala tympani 158. The electric field (159) applied through the implanted device is shown in long curved lines bending to the right, driving release of molecules of the administered compound (small, hollow circles).

Also shown in FIGS. 5A-5C is the outer wall 149 of the cochlea 140. As noted above with reference to FIGS. 3 and 4, the outer wall 149 includes numerous blood vessels 148 which provide a substantial vascular supply to the tissue of the cochlea 140. In FIG. 5C, the hollow arrows on the right of the figure show the direction of release of the compound crossing membranes.

Determining the Degree of Permeability of the Blood Labyrinth Barrier and the Concentration of Inflammatory Cytokines at the Blood Labyrinth Barrier Methods are provided for determining the degree of permeability of the BLB, one of the components in the process of modulating the BLB. In some embodiments, permeability of the BLB can be determined by systemic administration of a compound or molecule that induces either a temporary hearing loss (e.g., salicylate), or a temporary balance disorder (e.g., the vestibular active drugs known as anticholinergics or antihistamines). If enough of the molecule or compound passes through the more permeable BLB to enter the labyrinth (the vestibular system), the subject typically will experience a hearing loss, dizziness, or lose the sense of balance. Hearing deficits can be measured as an increase in pure tone audiogram thresholds, an increase in auditory brainstem response (ABR) thresholds; and/or a decrease in optoacoustic emissions (a distortion-product acoustic emission, or DPOAE) using methods that are well known in the art. Hearing or balance disorders, e.g., dizziness, also can be ascertained by asking the patient to report such perceptions or, in the case of a balance disorder, to perform a certain balancing task and to compare the performance to prior episodes. One may also track the patient's eye movements, and/or by use a gyroscope or accelerometer.

In other embodiments, the permeability of the BLB can be noninvasively and visually determined using contrast-enhanced, fluid attenuated inversion recovery magnetic resonance imaging (CE-FLAIR MRI), a technique well known in the art for determining BBB breakdown (Wardlaw et al., 2009; Ivens et al., 2010; Merino et al. 2013; Lee et al., 2017).

In other embodiments, leakiness can be further characterized by comparing a measure of permeability to that in the normal, less permeable, normal state. Hearing intensity or changes in a person's sense of balance over time, for example, can be measured and tracked. In still other embodiments, the methods involve examination of the timing between systemic or local administration of a molecule (such as salicylate) and the point when a detectable (threshold) concentration of the molecule has amassed in the labyrinth, i.e., behind the BLB. Comparing the results to those of a standard "normal" range control could inform a caregiver about the extent of permeability of the patient's BLB.

The location of the sensor used to measure the concentration behind the BLB and the extent of BLB permeability may be correlated with the frequencies affected. For example, if a patient experiences hearing loss in the low frequency range, e.g., below 1 kHz, the BLB may be leaking primarily in the apical turns of the cochlea where transmission of low frequencies occurs. Individual biosensors may be yield varied results depending on placement location, suggesting the need for multiple sensors on a single component of a medical device positioned within the cochlea, collecting data at individual locations simultaneously; alternatively, multiple biosensors could be placed at various locations in a sequential data collection scheme.

Further embodiments include methods involving the serial administration of molecules with similar relevant effects as salicylate or vestibular-active molecules, as described previously, but having a variety of different sizes and/or polarities. In one embodiment, molecules ranging in size from 1 to 1000 nm (or, e.g., less than 500 to 900 Da), are administered in series, largest to smallest, until a detectable (measurable) change in hearing or balance occurs. The leakiness can be characterized in terms of the largest molecule that could pass the BLB and elicited the effect. Similarly, in another embodiment, molecules ranging in polarity are administered in series, greatest to least, until a detectable change in hearing or balance occurs. Leakiness is characterized in terms of the most polar molecule that elicited the effect.

In other embodiments a series of molecules of a combination of different sizes and polarities may be administered (e.g., TPSA of 0-200, or W LOG P of −5 to 8). The sizes and polarities can be altered by selecting different types of active molecules, or by attaching the same active molecule to each of any number of different molecules, creating conjugated or fused (fusion) molecules of different sizes and polarities. Conjugated molecules such as fusion proteins or peptide/nucleic acid complexes are used in research and medicine, and are further discussed below (see, e.g., U.S. Pat. No. 10,301,629)

In yet other embodiments, methods are provided that do not require the pharmaceutical inducement of temporary or permanent hearing or balance impairments to evaluate the permeability of the BLB. In some embodiments a biosensor is implanted into the labyrinth so that the sensory aspect of the biosensor is in contact with the fluids (perilymph and/or endolymph compartments), and is capable of measuring the concentration of a pharmaceutical formulation administered systemically or locally to the middle ear that has passed to the labyrinth due to increased permeability of the BLB. In some embodiments, the biosensor can be a component of an implanted medical device, such as a cochlear implant.

In some embodiments disclosing methods limited to determining the permeability of the BLB (and not also for therapeutic, BLB modulating purposes), the pharmaceutical formulation does not naturally occur in blood. In other embodiments, the pharmaceutical formulation used for this purpose may naturally occur in blood but at a low enough concentration that it does not saturate the biosensor(s). Taking account of the pharmacokinetics of the pharmaceutical formulation administered, the concentration of the formulation in the labyrinth, will represent a direct measure of the permeability of the BLB. Examples of pharmaceutical formulations that may be used in some of these embodiments include barium, iodine, gold, gadolinium, fluorescein, and small molecular drugs such as corticosteroids. Example 1 describes the use of fluorescein to determine the degree of permeability of the BLB.

Further embodiments of methods for determining the permeability of the BLB involve detecting a change in electrical conductivity in the labyrinth using an intra-cochlear electrode. Changes to the electrical conductivity of the perilymph and endolymph (ionic) fluids take place when a pharmaceutical formulation is systemically or locally administered, passes through a more permeable BLB and, as a result, changes the ionic environment to become less conductive.

In one embodiment of a method to determine BLB permeability, the electrodes of a cochlear implant are used in a patient receiving the implant; no modification to the existing electrodes would be required for them to detect the change in conductivity. In other embodiments, cochlear implant electrodes may be modified, for example, to alter the conductivity of the fibrotic sheath encapsulating the electrode. In yet other embodiments the formulation, having crossed the leaking BLB, changes the conductivity of another component in the current path between (i) intra-cochlear electrode contacts, or (ii) intra- and extra-cochlear electrode channels. Inflammation of the cochlea is hypothesized to cause an increase in impedance measured using a cochlear implant electrode. Hence, in some embodiments, suitable pharmaceutical formulations include those that can produce local inflammation of the cochlea when administered systemically, such as lipopolysaccharide (LPS), keyhole limpet hemocyanin (KLH), histamine or bradykinin.

In some embodiments, the formulation is administered to the desired inner ear region by injection, catheter, through a refillable reservoir, or as part of intra-cochlear or intra-vestibular implant (e.g., cochlear implant electrode or other component), or as another such implant or device, whether as a "stand-alone" device or as a component of another implant or device. In all such embodiments in which a formulation is administered into the inner ear and measured in blood or other fluids/tissues, standard practices would be employed for sampling (blood draws) and evaluating samples traditional blood analysis methods or lab-on-chip technology can be employed. In embodiments in which in vivo analysis is to be conducted in blood or other fluids/tissues, biosensors may be used for short- or long-term sampling and analysis.

Some of the embodiments described above may include methods that may be incorporated into a fully or partially automated control system as described below. For some embodiments disclosed, methods may be combined with treatments for other conditions or diseases of the patent.

Modulating the BLB by Administering a Pharmaceutical Formulation

The embodiments of methods and pharmaceutical formulations disclosed to modulate the BLB may further be used in any known, broader method to monitor or treat a recipient of a CI or other medical device implanted in the inner ear. In some embodiments, the implanted device disclosed herein may be used as a component in a known control system that describes the monitoring or treatment of a CI recipient. In other embodiments the pharmaceutical formulation may be used in such a control system, for example the system disclosed in US20210001113 A1 for addressing hearing loss of CI recipients.

In some embodiments, the known control system in which the disclosed embodiments are used may be fully automated. In some embodiments, a single implanted medical device may be employed to modulate the BLB and may have multiple internal components hard wired for intra-device communication. In other embodiments, wireless technology may link various components of the device to a computer or other control device for communication of collected data. In still other embodiments a combination of hardwiring and wireless technologies may be used. In some embodiments the method of modulating the BLB may be implemented in a clinical or hospital setting; in other embodiments, the method may be implemented remotely.

In some embodiments the medical device used to modulate the BLB provides reports on demand for the current procedure or longer-term progress reports providing an historical record of the recipient's progress for the patient's electronic medical record.

Other Properties of the BLB: Increased Number of Transport Vesicles and Expression of Inflammatory Cytokines in a Growing Immune Response to Disruption or Injury of the BLB.

Permeability is one of the properties of the BLB that can be evaluated and modulated, but other properties, characteristics or features of the BLB can also be evaluated and modulated. Data from a histological analysis of Electron Micrographs (EMs) of the BLB in diseased (Meniere's) and normal states show that in patients with advanced Meniere's disease, increased permeability of the BLB is likely confirmed by obvious physical changes in the cells of the BLB (Ishiyama et al., 2017). While the tight junctions between endothelial cells comprising the walls of the capillaries and the BLB seem to remain intact (Id.) in Meniere's, the increased permeability of the BLB is underscored by the significantly greater number of transport vesicles present in the vascular endothelial cells, as well as the pericyte process detachment, and the disruption of the perivascular basement membrane surrounding the endothelial cells (Id.). These changes lead to a loss of BLB integrity.

The increased number of transport vesicle in the diseased state, coupled with known increased permeability of the BLB in these individuals suggest that caveolin-1 may be a likely target for modulating the BLB; by reducing the effect of caveolin-1 in the development of transport vesicles, the increased permeability of the BLB can be attenuated. Further, as an inflammatory response mounts following an injury or irritation at the barrier, such as that experienced by some CI recipients at implantation, the production of inflammatory cytokines may also be important targets for modulating the BLB; reducing the inflammatory response by cells of the BLB and surrounding tissues could have a protective effect on those very cells. Since the immune response itself damages the BLB, inflammatory cytokines may contribute to the damage and, thus, the increased permeability of the BLB, reducing its integrity further.

In some method embodiments administration of a pharmaceutical formulation comprising one or more compounds having or producing anti-pneumolysin activity reduces the immune response at the BLB, protecting it against further degradation from inflammatory cytokines.

In other embodiments, administration of a pharmaceutical formulation comprising one or more compounds having or producing anti-caveolin-1 activity may reduce the overproduction of transport vesicles in BLB cells, attenuating the increased permeability of those cells and preserving or boosting BLB integrity. In some embodiments, the compounds or molecules having or producing anti-caveolin-1 activity or anti-pneumolysin activity are nucleic acids such as, for example, siRNA, which, when bound to a vector that facilitates its entry into cells and nuclei, can suppress expression of proteins involved in the development of vesicles (in the case of anti-caveolin-1 activity) or in the production of cytokines in a building immune response (in the case of anti-pneumolysin activity), modulating these BLB properties.

Similarly, in some embodiments are provided pharmaceutical formulations comprising compounds or molecules having or producing activity directed toward blocking caveolin-1 receptors, or suppressing caveolin-1 over-expression.

In some method embodiments, pharmaceutical formulations comprising compounds or molecules having or producing anti-caveolin-1 activity or anti-pneumolysin activity are administered to reduce the activity or expression of target compounds or molecules such as inflammatory cytokines (e.g., such as TNF-$\alpha$, IL-6 and IL-1$\beta$) or genes involved in the production of transport vesicles in the endothelial and pericyte cells of the BLB, thereby modulating properties of the BLB. In other embodiments, the concentrations or activities of target molecules and compounds are measured using a medical device such as a CI, containing a biosensor. In some embodiments the biosensor is the device's electrode. In other embodiments the device contains one or more separate biosensors. In some embodiments the device is a component that functions to modulate properties of the BLB as part of a control system known in the art.

A person of ordinary skill in the art can appreciate that BLB properties other than those discussed herein can be similarly modulated using other pharmaceutical formulations in the disclosed method embodiments.

Pharmaceutical Formulations and their Preparation

Single compounds or molecules as well as the combinations of active and nonactive compounds including biologically active molecules and compounds, together with all other components that may be required to formulate a particular form (tablet, liquid, gel, etc.) for a particular mode of administration to deliver a therapeutically effective amount are collectively and generally referred to in this disclosure as "pharmaceutical formulations" The term "compound" or "agent" may also refer to any single component that comprises a pharmaceutical formulation. Pharmaceutical formulations or "formulations," as that term is used, are administered to modulate properties of the BLB and, specifically may act to reduce inflammation and/or otherwise modulate the permeability of the BLB and its surrounding tissues. If inflammation is the result of injury at the site of implantation of a medical device such as a CI, in preferred method embodiments, the attenuation of increasing inflammation over the days that ensue is a primary goal.

In some embodiments disclosed, one or more pharmaceutical formulations are administered to modulate the BLB such that if it is more permeable than it should be, it becomes less permeable or "leaky." These formulations include, among others: (i) vasoconstrictors (e.g., alpha-adrenoceptor agonists, vasopressin analogs, epinephrine, norepinephrine, phenylephrine (Sudafed PE), dopamine, dobutamine, migraine and headache medications (serotonin 5-hydroxytryptamine agonists or triptans)); (ii) corticosteroids (e.g., dexamethasone, bethamethasone, (Celestone), prednisone (Prednisone Intensol), prednisolone (Orapred, Prelone), triamcinolone or triamcinolone-acetonide (Aristospan Intra-Articular, Aristospan Intralesional, Kenalog), and methylprednisolone (Medrol, Depo-Medrol, Solu-Medrol)); (iii) compounds or molecules that have or produce anti-pneumolysin activity to address bacterial-mediated disruption of the BLB; and (iv) compounds or molecules that have or produce anti caveolin-1 activity, blocking caveolin-1 receptors, or suppressing caveolin-1 over-expression. In preferred embodiments, the pharmaceutical formulation comprises compounds from two or more of these four categories. A person of ordinary skill in the art of pharmaceuticals will appreciate that the prodrug form of any of the above-listed pharmaceuticals may be used for any of the disclosed embodiments as may be necessary to prepare one or more pharmaceutical formulations and/or use such formulations in the method embodiments disclosed to modulate the BLB.

In other embodiments disclosed, one or more pharmaceutical formulations are administered to modulate properties of the BLB such that a more permeable state is desired, e.g., for a research project. In some of these embodiments the BLB is deliberately disrupted or destabilized by administration of the formulation. Examples of such destabilizing formulations include, among others: salicylate, lipopolysaccharide (LPS), keyhole limpet hemocyanin (KLH), and a variety of vestibular-active molecules, such as anticholinergics and antihistamines, as well as other membrane destabilizing proteins or peptides known in the art (see, e.g., Fernandez et al., 2009). For example, LPS has been shown to induce systemic inflammation, compromising the BLB (Hirose et al., 2014).

In the disclosed embodiments, pharmaceutical formulations may comprise any single or combination of the following: biological substances, bioactive substances, conjugated or fusion molecules or compounds, viral and non-viral vectors, natural, synthetic and recombinant molecules, antibodies and antibody fragments, etc., pharmaceutical agents/ active pharmaceutical ingredients (APIs) including commercially available versions of the same, genes, nucleases, endonucleases, nucleic and ribonucleic acids such as messenger RNA (mRNA), siRNA and miRNA, naked DNA, DNA vectors, oligonucleotides, antisense polynucleotides, peptides, polypeptides, proteins including binding proteins, anti-oxidants, and signalling compounds that promote recovery and resolution, other chemicals, ions, and other molecules used to modulate inflammation within the body of individual. A person of ordinary skill in the art will appreciate that each if these substances can be generated by methods known in the art.

Conjugated molecules are, as the name suggests, molecules linked together to form a complex, which can be administered for treating a wide variety of disorders and diseases. These molecules are characterized by having a cell-permeable (or -penetrating) component that facilitates delivery of another, linked component, a molecule or compound with biological activity, to intracellular or intranuclear sites of action where they may elicit a variety of effects, including, e.g., among other things, the regulation of gene expression through interference with post-transcription processes. Some conjugated molecules have been used for facilitated transport of bioactive molecules across the BBB and BLB, and similarly may be used for applications at the BRB. Numerous types of vectors can be used to deliver and express one or more therapeutic molecules in target cells.

Small interfering RNA (siRNA) molecules are a prime example of an active molecule that can be delivered, as a complex with a vector, to a target cell. While the high molecular weight and negative charge of double-stranded siRNA molecules would prevent them from crossing the BLB, siRNA molecules have been coupled to vectors to facilitate transport to sites difficult to access. In one instance, labeled siRNA was delivered to inner ear cells by coupling it to a non-viral vector and injecting it into the middle ear where it permeated the round window member and gained access to inner ear cells of various kinds (Qi et al., 0214). These conjugated molecules have the potential to modulate the permeability and potentially several other properties of the BLB as well. siRNA molecules have been used successfully to modulate the BLB by interfering with the production of connexin 43, an important protein constituent of the tight junctions between endothelial cells of the BLB; connexin 43 is involved with the regulation of BLB integrity (Zhang et al., 2020). siRNA molecules further have been used in intracochlear gene therapy research (in mice) to target allele suppression to slow the progression of hearing loss (Yoshimura et al., 2019).

In certain aspects, inhibition of, e.g., expression of inflammatory cytokines can be achieved by administration of pharmaceutical formulations comprising inhibitory nucleic acids (e.g., dsRNAs, siRNAs, antisense oligonucleotides, etc.) directed to inhibit cytokine expression or activity. In some embodiments, pharmaceutical formulations comprise siRNA molecules coupled with transporter proteins or other molecules to facilitate entry into cells and nuclei, including those of the cells comprising the BLB. In one embodiment the transporter protein (coupled to an siRNA molecule) is one that is recognized by a BLB cell surface receptor, enabling endocytosis. In other embodiments one or more siRNA molecules comprise the pharmaceutical formulations. In yet other embodiments, the pharmaceutical formulation comprises one or more conjugated molecules, which each comprise one or more corticosteroids, vasoconstrictors, or compounds/molecules that have or produce either anti-pneumolysin activity or anti-caveolin-1 activity. In some method embodiments, such pharmaceutical formulations are prepared and administered to modulate permeability and possibly other properties of the BLB. In certain method embodiments, the pharmaceutical formulations comprising inhibitors of pneumolysin activity or caveolin-1 activity are administered such that activity of the target compounds is decreased by 5%, 10%, 15%, 20%, 25%, 30%, 35%, 40%, 45%, 50%, 55%, 60%, 70%, 80%, 90%, 95%, 96%, 97%, 98%, 99% or 100% compared to baseline control.

In certain method embodiments for modulating the BLB, the concentration of inflammatory cytokines at the BLB is decreased by administering pharmaceutical formulations comprising a corticosteroid such as dexamethasone. Such formulations may be systemically administered in an amount sufficient to provide a suitable, final dexamethasone concentration in the perilymph.

In certain method embodiments for modulating the BLB, expression of inflammatory cytokines at the BLB is decreased by systemically administering pharmaceutical formulations comprising one or more compounds having or producing anti-pneumolysin activity. Such formulations may be systemically administered in an amount sufficient to give a final formulation concentration in the perilymph in the range from about 20 pM to about 1200 μM, from about 70 pM to about 1200 μM, from about 100 pM to about 1000 μM, from about 150 pM to about 800 μM, or from about 250 pM to about 600 μM. In some embodiments such formulations are administered systemically; in other embodiments the formulations are administered locally to the middle or inner ear using methods described herein.

In certain method embodiments for modulating the BLB, expression of inflammatory cytokines at the BLB is decreased by administering pharmaceutical formulations comprising one or more compounds having or producing anti-caveolin-1 activity. Such formulations may be systemically administered in an amount sufficient to give a final formulation concentration in the perilymph in the range from about 20 pM to about 1200 μM, from about 70 pM to about 1200 μM, from about 100 pM to about 1000 μM, from about 150 pM to about 800 μM, or from about 250 pM to about 600 μM. In some embodiments such formulations are administered systemically; in other embodiments the formulations are administered locally to the middle or inner ear using methods described herein.

In some embodiments of pharmaceutical formulations, an siRNA molecule may be coupled with a transport molecule for targeting and suppressing caveolin-1 overexpression and, thus, in embodiments of methods incorporating such pharmaceutical formulations for modulation of (here, reduced permeability of) the BLB, it may reduce the transport of molecules from the blood through cells of the BLB. In still other embodiments pharmaceutical formulations comprising siRNA molecules are administered target the expression of immune system actors such as TNF-α, IL-1β and other cytokines responsible for the immune response to injury or irritation, i.e., those having anti-pneumolysin activity. In some pharmaceutical formulation embodiments, the siRNA molecules may be protected from degradation by being packaged in known non-viral nano-particle-based carrier systems, or encased in polymers, silica, porous silicon or lipids, for example (Kim et al., 2019). Pharmaceutical formulation embodiments may be combined with other such embodiments to be implemented in one or more disclosed method embodiments to modulate BLB properties, or specifically, BLB permeability.

Further, in some embodiments known gene editing technology may be used to excise or replace sections of genes that, e.g., encode regulators or cytokine availability at the BLB and surrounding tissues. For example, in some embodiments, gene editing strategies employing the various technologies known in the art, including but not limited to the CRISPR/cas9 system, among others, are used to correct genetic disorders to the extent such disorders manifest as permeable BLB (and other barrier) malfunctions. A person of ordinary skill in the art would appreciate that other gene editing technologies known in the art may be used in such embodiments, and other Cas or other enzymes, proteins or peptides may be functional in the Cas9 role. Gene editing methods known in the art can be performed upon the cells of a subject in vivo (or ex vivo and then administered as a component of a pharmaceutical formulation in the disclosed embodiments). Stem cell therapies may further be used to generate components of pharmaceutical formulation embodiments.

In some embodiments of pharmaceutical formulations, those comprising one or more compounds having or producing anti-caveolin-1 activity and/or anti-pneumolysin activity are effective for modulating the permeability and possibly other properties to improve BLB integrity. In other method and pharmaceutical formulation embodiments, combinations comprising any two or more of corticosteroids, vasoconstrictors and compounds having or producing anti-caveolin-1 activity and/or anti-pneumolysin activity in any form may be administered simultaneously or in serial by any single or combination of modes of administration to modulate the permeability of the BLB. Such embodiments may be used as a part of treatment regimens involving monitoring and preventing inflammation due to the increased expression of cytokines at or near the BLB and resulting loss of BLB integrity.

To prepare the pharmaceutical formulations according to the disclosed embodiments, a therapeutically effective amount of one or more of the compounds or formulations according to the disclosed embodiments are preferably intimately admixed with a pharmaceutically acceptable carrier, diluent, or excipient, according to conventional pharmaceutical compounding techniques to produce a dose. The term "pharmaceutically acceptable carrier diluent or excipient" refers to any substance, not itself a therapeutic agent, used as a carrier or vehicle, or nonactive component of the formulation for administration to an individual, or added to a pharmaceutical composition to improve its handling or storage properties, or to permit or facilitate formation of a unit dose of the composition, and that does not produce unacceptable toxicity or interaction with other components in the composition.

The amount of formulation included within therapeutically active formulations according to the disclosed embodiments is an effective amount for affecting the desired outcome, i.e., modulation of the BLB. The concentrations or activities of compounds or formulations measured in blood or other fluids is known in the art. See, e.g., Rafai et al. [2017] *Tietz textbook of clinical chemistry and molecular diagnostics* ($6^{th}$ ed.) St. Louis: Elsevier.

The choice of pharmaceutically acceptable carrier, excipient or diluent may be selected based on the formulation and the intended route of administration, as well as standard pharmaceutical practice. Such compositions may comprise any agents that may aid, regulate, release, or increase entry into the body compartment, tissue, intracellular or intranuclear target site, such as binder(s), lubricant(s), suspending agent(s), coating agent(s), solubilizing agent(s), or other agents. Nonlimiting examples include polymers and silicones. Administration of an implant of a formulation for the sustained release may also be used to obtain prolonged exposure and action, and in some embodiments may be, e.g., a liquid, gel, or solid implant or may be in the form of particles, including nanoparticles. The term "sustained release" refers to formulations from which the formulation is released at a slow rate allowing for a longer period of exposure at active concentrations. Intramuscular and subcutaneous administration generally involves injection of the pharmaceutical formulation until it forms a deposit from which the formulation can be released in a sustained fashion. A refillable reservoir or deposit (or depot) may also be used, e.g., in the middle ear, from which the formulation is dispensed. Further, a number of technologies have been developed to permit sustained release of formulations injected into the ear for transfer through the round window membrane, including implantation of an osmotic or digital minipump (Wimmer et al., 2004); hyaluronic acid liposomal gel (El Kechai et al., 2016); a film-forming agent and microspheres containing, e.g., corticosteroids (Dormer et al., 2019) a combination nanotechnology-hydrogel delivery system (Li et al., 2017).

A carrier may take a wide variety of forms depending on the form of preparation desired for administration, e.g., including solutions, gels, films, particles, powders, creams, ointments, lotions, transdermal patches (some of which may be further formulated as sustained release preparations).

In some embodiments, the active compound is included in the pharmaceutically acceptable carrier or diluent in an amount sufficient to deliver to a recipient a therapeutically effective amount for the desired indication, without causing serious toxic effects or being cleared from the system before it can reach its intended site of action.

Modes of Administration

Approaches to the delivery of pharmaceutical formulations include but are not limited to localized administration/delivery approaches where the pharmaceutical formulations are initially delivered at or near a target location within the recipient. The goal of localized delivery is that only the target location, and possibly a small amount of surrounding tissue, is exposed to the pharmaceutical formulation. Thus, pharmaceutical formulations are delivered at the specific target location and may remain in a proximity of the target location. In some embodiments, the pharmaceutical formulation may be introduced into the body via an outlet of the catheter, which is positioned at the target location within the recipient. An example of such localized delivery of a pharmaceutical formulation may occur, for example, by inserting in the femoral artery of the thigh a catheter and guiding it to a specific location where the formulation will be released to act locally, such as in the arterial supply to the cochlea, or into the cranium. Another example is injecting a liquid or gel formulation into the middle ear for absorption through the round window membrane into the inner ear labyrinth. In some embodiments, the formulation may be locally deposited in the middle ear in the form of a gel-based or liquid-based composition, allowing transport from the delivery site to the more permeable BLB via the cochlea.

In other embodiments, delivery approaches may include intra-cochlear delivery introduced via a cochlear implant electrode array, or by injection into the cochlea.

In some embodiments, the pharmaceutical formulation may be delivered locally by injection or infusion into the labyrinthine artery or cochlea/vestibule supply artery, where microparticles or nanoparticles accumulate at an appropriate site, e.g., they may gather in the microcapillaries or at the more permeable (i.e., leaky) BLB.

In other circumstances, pharmaceutical formulations may be delivered to a recipient using a systemic administration approach. With systemic delivery, the pharmaceutical formulation is introduced into the circulatory system of the recipient so that the entire body of the recipient is exposed to the pharmaceutical formulation(s). Systemic administration of pharmaceutical formulations can take place via, e.g., enteral administration (absorption of the drug through the gastrointestinal tract) or parenteral administration (generally injection, infusion, or implantation).

Systematic and localized modes of pharmaceutical formulations administration have their advantages, as well as drawbacks that may limit its use for certain recipients, disorders, diseases, etc. The goal of localized administration is to direct the release of the formulation to only the target location; a small amount of surrounding tissue may be exposed to the formulation's effect. The fact that the pharmaceutical formulation is delivered at or near the target location is advantageous in that, e.g., a relatively high concentration of the formulation may be administered to the target location as the rest of the recipient's body has limited exposure to it. Localized administration suffers from the problem that certain areas of a recipient's body are difficult to access in a manner that allows for the direct delivery of the pharmaceutical formulation.

In the context of the inner ear, localized administration may not pose the risk of systemic toxicity, but it may be more difficult as the inner ear, and in particular, the apical region of a recipient's cochlea, is difficult to access. Moreover, injecting a pharmaceutical formulation into the cochlea may cause the loss of residual hearing due to disruption of the BLB, e.g., through destruction of hair cells, forming an opening the cochlea that changes the cochlear dynamics, and other effects. In some embodiments, administration of a pharmaceutical formulation to the perilymph or endolymph compartments may include any of the following known methods: (i) via injection or deposition of the formulation at the round window membrane, or through a cochleostomy to the scala tympani; (ii) through a direct cochleostomy to the scala media; (iii) using a combination of those two pathways; (iv) implanting a CI with drug-eluting electrodes (through a polymer, silica, silicone or other coating, or delivered through a separate delivery cannula associated with the electrode, or other similar delivery channel); and (v) a less invasive, newer approach: systemic transfer of, e.g., a gene (Wang et al., 2018).

As referenced above, a drawback of systemic administration is that almost all tissues of the body are exposed to the pharmaceutical formulations administered in this way. Accordingly, systemically administered pharmaceutical formulations must be relatively harmless to the body, and further, must be administered to achieve a low enough concentration to prevent inducing unwanted side effects outside of the intended target location. However, systemic administration is easier to administer than is local administration, especially to the middle or the inner ear areas, and has the potential reach nearly all tissues if a whole-body approach is needed.

The choice of systemic or local administration must be informed by the pharmacokinetics of the pharmaceutical formulation being administered. A person of ordinary skill will appreciate the impact pharmacokinetics will have on the mode of administration, the dose, the timing, and duration of treatment. Several excellent reviews and discussions are available regarding local (middle/inner ear) pharmacokinetics of various pharmaceutical agents (see, e.g., Plontke et al., 2017; Salt 2005; Nyberg et al 2019; Salt and Plontke 2018; Rybak et al., 2019; and McCall et al., Drug delivery for treatment of inner ear disease: current state of knowledge. *Ear and hearing* vol. 31(2): 156-65, 2010. doi: 10.1097/AUD.0b013e3181c351f2).

In the context of the inner ear, systemic administration may be problematic as noted, as it is difficult to deliver pharmaceutical formulations in effective concentrations needed for the cochlea without inducing unacceptable toxic levels at other areas of the body (e.g., the pharmacokinetics limits the ability to deliver the drug to a specific location, such as high in the apex of the cochlea). That is, systemic administration of pharmaceutical formulations to the inner ear may require such low concentrations (to prevent systemic toxicity) as to render the pharmaceutical formulations largely ineffective for inner ear treatment.

Some of the methods presented herein are primarily described with reference to a specific implantable medical device system, namely, a cochlear implant system. However, a person of ordinary skill in the art would appreciate that the methods disclosed also may be used with other types of implantable medical devices or implantable medical device systems. For example, the methods presented herein may be used with other auditory prosthesis systems and related devices. The methods and pharmaceutical formulations disclosed herein may also be used with tinnitus therapy devices, vestibular devices (e.g., vestibular implants), visual devices (i.e., bionic eyes), sensors, pacemakers, drug delivery systems, defibrillators, functional electrical stimulation devices, catheters, seizure devices (e.g., devices for monitoring and/or treating epileptic events), sleep apnea devices, electroporation devices, and others.

The pharmaceutical formulations of the embodiments or modifications thereto can be administered in any number of ways, e.g., without limitation, by any one or more of the following: (1) inhalation; (2) in the form of a suppository or pessary; (3) in the form of a topical lotion, solution, cream, ointment or dusting powder; (4) by use of a transdermal patch; (5) orally in the form of tablets containing excipients such as starch or lactose, or in capsules or ovules, micro- or nanoparticles, either alone or in admixture with excipients, or in the form of elixirs, solutions or suspensions containing flavoring or coloring agents; (6) for ophthalmic or auditory disorders and diseases, they may be formulated as drops or a solution, gel or other form for injection or use in a reservoir; (7) for parenteral administration (any route of administration that does not involve absorption via the gastrointestinal tract), they may be administered intravenously, intramuscularly, intracavernosally or subcutaneously, or inhaled or other intranasal administration in the form of a sterile aqueous solution or injectable implant or (micro-/nano-) particles, or inhalable substances that may contain other substances, e.g., with adequate salt or monosaccharide content to make the solution isotonic with blood or with substances that allow sustained release, such as micro- or nano-particles or a gel; and (8) for enteral administration (entry to the circulatory system via absorption through the gastrointestinal tract) of the compositions may be administered in the form of tablets, gels, solutions, lozenges, semi-solids and any other edible or insertable forms, which can be formulated in a conventional manner according to known methods in the art.

In disclosed embodiments, any suitable mechanism of delivery may be used to systemically introduce the pharmaceutical formulation for modulation of the BLB. In one embodiment, localized release of a systemically circulating pharmaceutical formulation is shown, using as a reference, a cochlear implant 100 and cochlea 140, as detailed with reference to FIGS. 2 and 4A-4C. As noted elsewhere, other devices may be used in keeping with the totality of this disclosure.

Doses and Schedules

One of ordinary skill in the art will recognize that in the disclosed embodiments a therapeutically effective amount provided in the formulation, as well as the dosing, and timing of dosing will depend on the condition being treated and its severity, the pharmaceutical formulation and its pharmacokinetics, the mode of administration, and other factors such as weight and condition of the patient, and the judgment of the prescribing caregiver, among other considerations.

In general, a therapeutically effective amount of the pharmaceutical formulations in dosage form usually ranges from less than about 0.001 mg/kg patient body weight to about 2.5 g/kg patient body weight on a per hour, day or other time period basis, regardless if those amounts are delivered in a single dose or apportioned over multiple periods of administration in the specified period. In the most preferred embodiments, pharmaceutical formulations according to the present invention are administered in a suitable carrier in amounts ranging from about 1 mg/kg to about 100 mg/kg per hour, day or per other period, again, regardless if those amounts are delivered in a single dose or apportioned over multiple periods of administration in the specified period.

In the disclosed, preferred embodiments, a therapeutically effective amount of the pharmaceutical formulation in dosage form is, based on an hourly, daily or other period basis, and dependent on the route of administration, among other things, usually less than about 0.001 mg/kg body weight, less than about 0.025 mg/kg, less than about 0.050 mg/kg, less than about 0.075 mg/kg, less than about 0.100 mg/kg, less than about 0.15 mg/kg, less than about 0.20 mg/kg, less than about 0.25 mg/kg, less than about 0.30 mg/kg, less than about 0.35 mg/kg, less than about 0.40 mg/kg, less than about 0.45 mg/kg, less than about 0.50 mg/kg, less than about 0.55 mg/kg, less than about 0.60 mg/kg, less than about 0.65 mg/kg, less than about 0.70 mg/kg, less than about 0.75 mg/kg, less than about 0.80 mg/kg, less than about 0.85 mg/kg, less than about 0.90 mg/kg, less than about 0.95 mg/kg, less than about 1.0 mg/kg, less than about 2.0 mg/kg, less than about 3.0 mg/kg, less than about 4.0 mg/kg, less than about 5.0 mg/kg, less than about 6.0 mg/kg, less than about 7.0 mg/kg, less than about 8.0 mg/kg, less than about 9.0 mg/kg, less than about 10.0 mg/kg, less than about 11.0 mg/kg, less than about 12.0 mg/kg, less than about 13.0 mg/kg, less than about 14.0 mg/kg, less than about 15.0 mg/kg, less than about 16.0 mg/kg, less than about 17.0 mg/kg, less than about 18.0 mg/kg, less than about 19.0 mg/kg, less than about 20.0 mg/kg, less than about 25.0 mg/kg, less than about 30.0 mg/kg, less than about 35.0 mg/kg, less than about 40.0 mg/kg, less than about 45.0 mg/kg, less than about 50.0 mg/kg, less than about 55.0 mg/kg, less than about 60.0 mg/kg, less than about 65.0 mg/kg, less than about 70.0 mg/kg, less than about 75.0 mg/kg, less than about 80.0 mg/kg, less than about 85.0 mg/kg, less than about 90.0 mg/kg, less than about 95.0 mg/kg, less than about 100 mg/kg, less than about 120.0 mg/kg, less than about 140.0 mg/kg, less than about 160.0 mg/kg, less than about 180.0 mg/kg, less than about 200.0 mg/kg, less than about 250.0 mg/kg, less than about 300.0 mg/kg, less than about 350.0 mg/kg, less than about 400.0 mg/kg, less than about 600.0 mg/kg, less than about 800.0 mg/kg, less than about 1.0 g/kg, less than about 1.5 g/kg, less than about 2.0 g/kg, less than about 2.5 g/kg, less than about 2.75 g/kg, ranges between about 0.10 mg/kg to about 1.25 mg/kg, ranges between about 0.10 mg/kg to about 0.50 mg/kg, ranges between about 0.20 mg/kg to about 0.40 mg/kg, ranges between about 0.20 mg/kg to about 0.60 mg/kg, ranges between about 0.30 mg/kg to about 0.70 mg/kg, ranges between about 0.40 mg/kg to about 0.80 mg/kg, ranges between about 0.50 mg/kg to about 0.90 mg/kg, ranges between about 0.60 mg/kg to about 1.0 mg/kg, ranges between about 0.90 mg/kg to about 1.10 mg/kg, ranges between about 1.00 mg/kg to about 1.30 mg/kg, ranges between about 1.10 mg/kg to about 1.5 mg/kg, ranges between about 1.25 mg/kg to about 1.75 mg/kg, ranges between about 1.5 mg/kg to about 2.0 mg/kg, ranges between about 1.75 mg/kg to about 2.25 mg/kg, ranges between about 2.0 mg/kg to about 2.5 mg/kg, ranges between about 2.0 mg/kg to about 5.0 mg/kg, ranges between about 3.0 mg/kg to about 7.0 mg/kg, ranges between about 5.0 mg/kg to about 10 mg/kg, ranges between about 10.0 mg/kg to about 20 mg/kg, ranges between about 20.0 mg/kg to about 30.0 mg/kg, ranges between about 30.0 mg/kg to about 40 mg/kg, ranges between about 40.0 mg/kg to about 50.0 mg/kg, ranges between about 50.0 mg/kg to about 60.0 mg/kg, ranges between about 60.0 mg/kg to about 70.0 mg/kg, ranges between about 70.0 mg/kg to about 80.0 mg/kg, ranges between about 80.0 mg/kg to about 90.0 mg/kg, ranges between about 90.0 mg/kg to about 100.0 mg/kg, ranges between about 100.0 mg/kg to about 110.0 mg/kg, ranges between about 110.0 mg/kg to about 120.0 mg/kg, ranges between about 120.0 mg/kg to about 130.0 mg/kg, ranges between about 130.0 mg/kg to about 140.0 mg/kg, ranges between about 140.0 mg/kg to about 150.0 mg/kg, ranges between about 150.0 mg/kg to about 160.0 mg/kg, ranges between about 160.0 mg/kg to about 170.0 mg/kg, ranges between about 170.0 mg/kg to about 180.0 mg/kg, ranges between about 180.0 mg/kg to about 190.0 mg/kg ranges between about 190.0 mg/kg to about 200.0 mg/kg, ranges between about 200.0 mg/kg to about 250.0 mg/kg, ranges between about 250.0 mg/kg to about 300.0 mg/kg, ranges between about 300.0 mg/kg to about 350.0 mg/kg, ranges between about 350.0 mg/kg to about 400.0 mg/kg, ranges between about 400.0 mg/kg to about 450.0 mg/kg, ranges between about 450.0 mg/kg to about 500.0 mg/kg, ranges between about 500.0 mg/kg to about 550.0 mg/kg, ranges between about 550.0 mg/kg to about 600.0 mg/kg, ranges between about 600.0 mg/kg to about 650.0 mg/kg, ranges between about 650.0 mg/kg to about 700.0 mg/kg, ranges between about 700.0 mg/kg to about 750.0 mg/kg, ranges between about 750.0 mg/kg to about 800.0 mg/kg, ranges between about 800.0 mg/kg to about 850.0 mg/kg, ranges between about 850.0 mg/kg to about 900.0 mg/kg, ranges between about 900.0 mg/kg to about 950.0 mg/kg, ranges between about 950.0 mg/kg to about 1.0 g/kg, ranges between about 1.0 g/kg to about 1.2 g/kg, ranges between about 1.2 g/kg to about 1.4 g/kg, ranges between about 1.4 g/kg to about 1.6 g/kg, ranges between about 1.6 g/kg to about 1.8 g/kg, ranges between about 1.8 g/kg to about 2.0 g/kg, ranges between about 2.0 g/kg to about 2.25 g/kg, ranges between about 2.25 g/kg to about 2.5 g/kg, ranges from about 2.5 g/kg to about 2.75 g/kg, ranges from about 2.75 g/kg to about 3.0 g/kg of body weight. Typically, a physician or other caregiver licensed to prescribe pharmaceuticals will determine the actual dosage most suitable for an individual subject, and it will vary by formulation and other factors, as referenced above.

All ranges and ratios discussed here can and necessarily do describe all values, subranges and sub ratios therein for all embodiments, and all such subranges and subtraction also form part and parcel of the disclosed embodiments. Any listed range or ratio can be easily recognized as sufficiently describing and enabling the same range or ratio being broken down into at least equal halves, thirds, quarters, fifths, tenths, etc. each range or ratio discussed herein can be readily broken down into a lower third, middle third and upper third, etc. Alternatively, a range of 1 to 50 is understood to include any number, fraction or combination of numbers from the group of positive numbers between about 0 and up to and including about 50.

In some embodiments two or more pharmaceutical formulations may be administered simultaneously; in other embodiments two or more pharmaceutical formulations may be administered serially. In still other embodiments two or more pharmaceutical formulations can be administered each through a different mode of administration (e.g., systemic, intracochlear, locally to the middle ear).

In certain method embodiments for modulating the BLB, the pharmaceutical formulation is administered once daily; in other embodiments, the compound is administered twice to six times daily; in yet other embodiments, the compound is administered once every two days, once every three days, once every four days, once every five days, once every six days, once every seven days, once every two weeks, once every three weeks, once every four weeks, once every two months, once every six months, or once per year. In other embodiments, the formulation is administered on an irregular basis. In still other embodiments, the formulation is administered on an as-needed basis, as determined through the closed control system.

In some embodiments, methods comprise the pharmaceutical formulation being administered for modulating the permeability of the BLB, which administration will extend for time periods of about 1 to 24 hours, 1 to 4 days, 3 to 6 days, 5 to 8 days, exceeding one week, two weeks, three weeks, one month, two months, three months, four months, five months, six months, 9 months, one year, two years, three years, four years, or five years, ten years, or fifteen years; or for example, any time period range in hours, days, months or years in which the low end of the range is any time period between 1 hour and 2 years, 2 to 10 years, 15 years, and the upper end of the range is between 15 days and 20 years (e.g., between 4 weeks and 15 years, between 6 months and 20 years). In some cases, it may be advantageous for the formulations of the disclosed embodiments and their modifications to be administered for the life of the patient.

Otic conditions typically are treated by administering multiple doses of drops or injections over several days and up to two weeks, sometimes with multiple doses administered daily. Pharmaceutical formulations of the embodiments disclosed herein may be re-administered at any desired frequency (e.g., daily, weekly, etc.) to achieve a suitable therapeutic effect. In some embodiments, the formulation may be delivered with a cochlear implant or during the cochlear implantation procedure. In other embodiments, the formulations may be delivered with any other type of middle or inner ear implant or device, or as a component of a known control system.

A person of ordinary skill in the art will appreciate that the dosing interval may need to be adjusted according to the needs of individual patients. In some embodiments involving longer intervals of administration, formulations may be administered in a form appropriate for sustained release, including the formation of depots for such release.

In preferred embodiments, the administration of pharmaceutical formulations remains effective for at least 12 hours, at least 1 day, at least 3 days, at least 1 week, two weeks, three weeks, one month, two months, three months, four months, five months, six months, one year, two years, three years, four years, or five years, ten years, fifteen years, twenty years, or for the remainder of the subject's life.

Modulation of BLB Properties to Treat Disorders and Diseases

In some method embodiments, pharmaceutical formulations may be administered ultimately to treat conditions, disorders and diseases arising from or involving dysfunction of the BLB.

In some embodiments, the methods and pharmaceutical formulations disclosed herein are used to treat patients with Meniere's disease.

The disclosed embodiments and modifications may be extended to treat age-related hearing loss or temporary cochlear implant-related hearing loss, e.g., by switching off or modulating the immune system by preventing endothelial cells and pericytes and other the cells, or the junctions between them, from becoming permeable to molecules and compounds that it otherwise would not let pass into the inner ear.

In some embodiments, the methods, pharmaceutical formulations and their modifications may be used in tandem with a control system known in the art that is partially or fully automated to modulate properties of the BLB, including its permeability, and to monitor and treat patients with disorders and diseases involving hearing impairments. In other embodiments, the methods and pharmaceutical formulations may be used to treat individuals with disorders and diseases that alter the permeability of other physiological barriers, such as the BRB and BBB.

The embodiments disclosed for methods of modulating the BLB can be used prophylactically, to prevent, reduce or delay the progression of hearing loss or other auditory disorders associated with loss of BLB or other inner ear function.

The embodiments disclosed of pharmaceutical formulations may be used alone or in combination with treatments or components of treatments for other conditions, disorders, or diseases. In some disclosed embodiments, methods and pharmaceutical formulations are used as a component in one or more treatment regimens.

Cochlear Implant System and Relevant Design Considerations

Figure 1B:
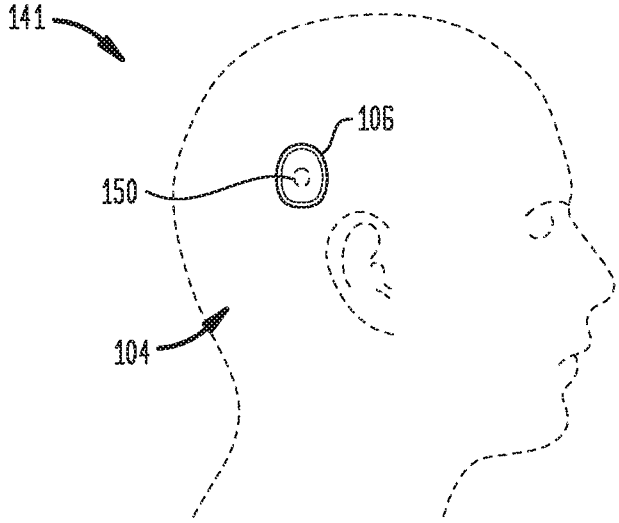
FIG. 1B is a side view of a recipient wearing a sound processing unit of the cochlear implant system of FIG. 1A.
Figure 1C:
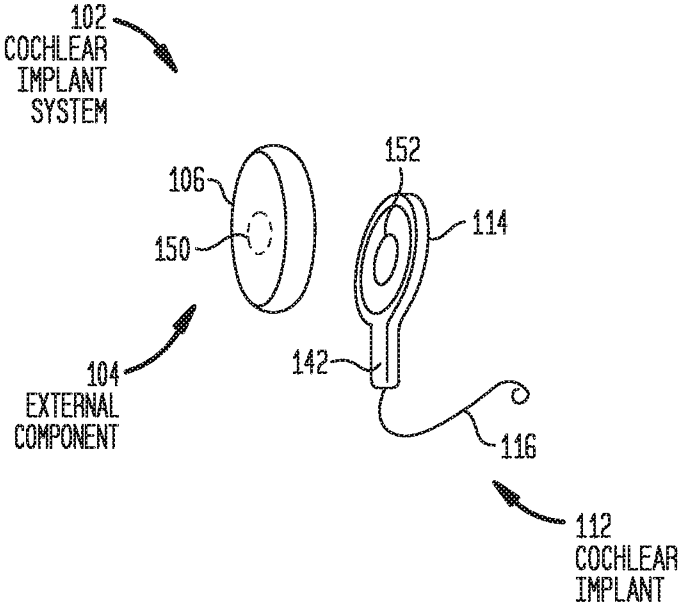
FIG. 1C is a schematic view of components of the cochlear implant system of FIG. 1A.
Figure 1D:
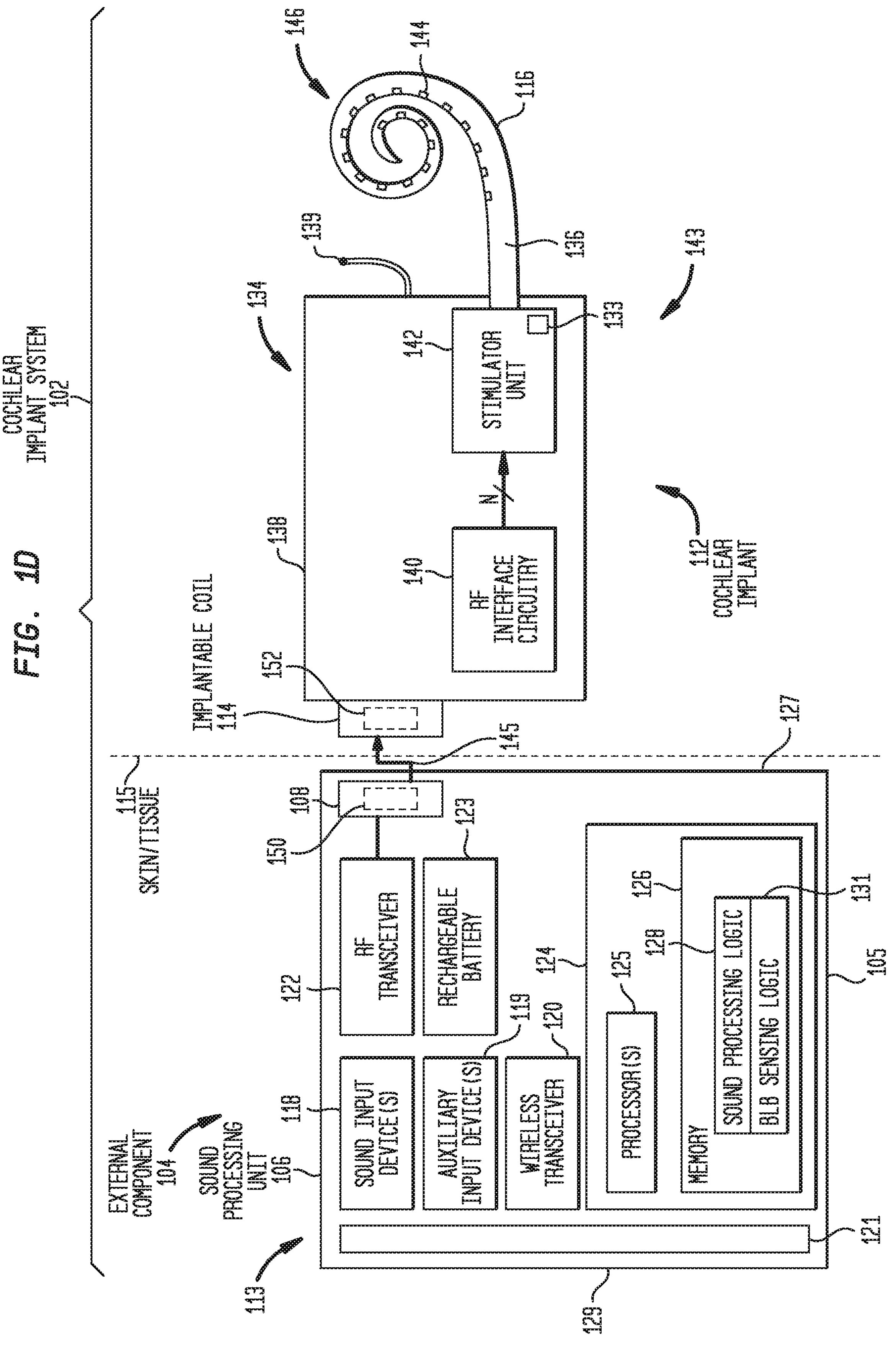
FIG. 1D is a block diagram of the cochlear implant system of FIG. 1A.

FIGS. 1A-1D are diagrams illustrating an example cochlear implant system 102 configured to implement certain embodiments of the control systems and methods presented herein. The cochlear implant system 102 comprises an external component 104 and an implantable component 112. In the examples of FIGS. 1A-1D, the implantable component is sometimes referred to as a "cochlear implant." FIG. 1A is a schematic diagram illustrating the implantable component 112 implanted in the head 141 of a recipient, while FIG. 1B is schematic drawing of the external component 104 worn on the head 141 of the recipient. FIG. 1C is another schematic view of the cochlear implant system 102, while FIG. 1D is a block diagram illustrating further details of the cochlear implant system 102. For ease of description, FIGS. 1A-1D will generally be described together.

As noted, cochlear implant system 102 includes an external component 104 that is configured to be directly or indirectly attached to the body of the recipient and an implantable component 112 configured to be implanted in the recipient. In the examples of FIGS. 1A-1D, the external component 104 comprises a sound processing unit 106, while the implantable component 112 includes an internal coil 114, a stimulator unit 142, and an elongate stimulating assembly 116 configured to be implanted in the recipient's cochlea.

In the example of FIGS. 1A-1D, the sound processing unit 106 is an off-the-ear (OTE) sound processing unit, sometimes referred to herein as an OTE component, that is configured to send data and power to the implantable component 112. In general, an OTE sound processing unit is a component having a generally cylindrically shaped housing 105 and which is configured to be magnetically coupled to the recipient's head (e.g., includes an integrated external magnet 150 configured to be magnetically coupled to an implantable magnet 152 in the implantable component 112). The OTE sound processing unit 106 also includes an integrated external coil 108 that is configured to be inductively coupled to the implantable coil 114.

It is to be appreciated that the OTE sound processing unit 106 is merely illustrative of the external devices that could operate with implantable component 112. For example, in alternative examples, the external component may comprise a behind-the-ear (BTE) sound processing unit or a micro-BTE sound processing unit and a separate external. In general, a BTE sound processing unit comprises a housing that is shaped to be worn on the outer ear of the recipient and is connected to the separate external coil assembly via a cable, where the external coil assembly is configured to be magnetically and inductively coupled to the implantable coil 114. It is also to be appreciated that alternative external components could be located in the recipient's ear canal, worn on the body, etc.

FIGS. 1A-1D illustrate an arrangement in which the cochlear implant system 102 includes an external component. However, it is to be appreciated that the disclosed embodiments and modifications may be implemented in cochlear implant systems having alternative arrangements. For example, embodiments presented herein can be implemented by a totally implantable cochlear implant or other totally implantable medical device. A totally implantable medical device is a device in which all components of the device are configured to be implanted under skin/tissue of a recipient. Because all components are implantable, a totally implantable medical device operates, for at least a finite period of time, without the need of an external device/component. However, an external component can be used to, for example, charge the internal power source (battery) of the totally implantable medical device.

Returning to the specific example of FIGS. 1A-ID, FIG. 1D illustrates that the OTE sound processing unit 106 comprises one or more input devices 113 that are configured to receive input signals (e.g., sound or data signals). The one or more input devices 113 include one or more sound input devices 118 (e.g., microphones, audio input ports, telecoils, etc.), one or more auxiliary input devices 119 (e.g., audio ports, such as a Direct Audio Input (DAI), data ports, such as a Universal Serial Bus (USB) port, cable port, etc.), and a wireless transmitter/receiver (transceiver) 120. However, it is to be appreciated that one or more input devices 113 may include additional types of input devices and/or less input devices (e.g., the wireless transceiver 120 and/or one or more auxiliary input devices 119 could be omitted).

The OTE sound processing unit 106 also comprises the external coil 108, a charging coil 121, a closely-coupled transmitter/receiver (transceiver) 122, sometimes referred to as or radio-frequency (RF) transceiver 122, at least one rechargeable battery 123, and a processing module 124. The processing module 124 comprises one or more processors 125 and a memory device (memory) 126 that includes sound processing logic 128 and sensing logic 131. The sensor may provide measurements in terms of the standard cochlear implant impedance measurement, NRT measurement, or ECochG measurement. The memory device 126 may comprise any one or more of: Non-Volatile Memory (NVM), Ferroelectric Random Access Memory (FRAM), read only memory (ROM), random access memory (RAM), magnetic disk storage media devices, optical storage media devices, flash memory devices, electrical, optical, or other physical/tangible memory storage devices. The one or more processors 125 are, for example, microprocessors or microcontrollers that execute instructions for the sound processing logic 128 and/or sensing t logic 131 stored in memory device 126.

The implantable component 112 comprises an implant body (main module) 134, a lead region 136, and the intra-cochlear stimulating assembly 116, all configured to be implanted under the skin/tissue (tissue) 115 of the recipient. The implant body 134 generally comprises a hermetically-sealed housing 138 in which RF interface circuitry 140 and a stimulator unit 142 are disposed. The implant body 134 also includes the internal/implantable coil 114 that is generally external to the housing 138, but which is connected to the transceiver 140 via a hermetic feedthrough (not shown in FIG. 1D). As shown in FIG. 1D, the stimulator can comprise sensing hardware 133, as described further below.

As noted, stimulating assembly 116 is configured to be at least partially implanted in the recipient's cochlea. Stimulating assembly 116 includes a plurality of longitudinally spaced intra-cochlear electrical stimulating contacts (electrodes) 144 that collectively form a contact or electrode array 146 for delivery of electrical stimulation (current) to the recipient's cochlea.

Stimulating assembly 116 extends through an opening in the recipient's cochlea (e.g., cochleostomy, the round window, etc.) and has a proximal end connected to stimulator unit 142 via lead region 136 and a hermetic feedthrough (not shown in FIG. 1D). Lead region 136 includes a plurality of conductors (wires) that electrically couple the electrodes 144 to the stimulator unit 142. The implantable component 112 also includes an electrode outside of the cochlea, sometimes referred to as the extra-cochlear electrode (ECE) 139.

As noted, the cochlear implant system 102 includes the external coil 108 and the implantable coil 114. The external magnet 150 is fixed relative to the external coil 108 and the implantable magnet 152 is fixed relative to the implantable coil 114. The magnets fixed relative to the external coil 108 and the implantable coil 114 facilitate the operational alignment of the external coil 108 with the implantable coil 114. This operational alignment of the coils enables the external component 104 to transmit data and power to the implantable component 112 via a closely-coupled wireless link formed between the external coil 108 with the implantable coil 114. In certain examples, the closely-coupled wireless link is a radio frequency (RF) link. However, various other types of energy transfer, such as infrared (IR), electromagnetic, capacitive and inductive transfer, may be used to transfer the power and/or data from an external component to an implantable component and, as such, FIG. 1D illustrates only one example arrangement.

As noted above, sound processing unit 106 includes the processing module 124. The processing module 124 is configured to convert received input signals (received at one or more of the input devices 113) into output signals for use in stimulating a first ear of a recipient (i.e., the processing module 124 is configured to perform sound processing on input signals received at the sound processing unit 106). Stated differently, the one or more processors 125 are configured to execute sound processing logic 128 in memory 126 to convert the received input signals into output signals 145 that represent electrical stimulation for delivery to the recipient.

As noted, FIG. 1D illustrates an embodiment in which the processing module 124 in the sound processing unit 106 generates the output signals. In an alternative embodiment, the sound processing unit 106 can send less processed information (e.g., audio data) to the implantable component 112 and the sound processing operations (e.g., conversion of sounds to output signals 145) can be performed by a processor within the implantable component 112. That is, the implantable component 112, rather than the sound processing unit 106, could include a processing module that is similar to processing module 124 of FIG. 1D.

Returning to the specific example of FIG. 1D, the output signals 145 are provided to the RF transceiver 122, which transcutaneously transfers the output signals (e.g., in an encoded manner) to the implantable component 112 via external coil 108 and implantable coil 114. That is, the output signals are received at the RF interface circuitry 140 via implantable coil 114 and provided to the stimulator unit 142. The stimulator unit 142 is configured to utilize the output signals to generate electrical stimulation signals (e.g., current signals) for delivery to the recipient's cochlea via "stimulation channels," where each stimulating channel comprises one or more of the electrodes 144. In this way, cochlear implant system 102 electrically stimulates the recipient's auditory nerve cells, bypassing absent or defective hair cells that normally transduce acoustic vibrations into neural activity, in a manner that causes the recipient to perceive one or more components of the received sound signals.

As noted above, cochlear implant system 102 includes BLB sensing hardware 133 and BLB sensing logic 131.

Biosensors that are available commercially or by custom design may be employed. Each may be (i) a stand-alone device; (ii) a component of the cochlear implant system 102 or its electrode(s); (iii) a component of any other intra-vestibular or intra-cochlear implant; or (iv) a component of any device for delivering pharmaceutical formulations into the middle ear, the inner ear labyrinth, e.g., the perilymph and/or endolymph compartments, or into other parts of the inner ear or vestibular system. Specifically, the biosensor(s) will be able to measure the concentration of at least one pharmaceutical formulation in a fluid, or, e.g., inference, such as a change in conductivity. For all embodiments involving determination of the permeability of the BLB by one or more biosensors and/or electrodes, the biosensors and/or electrodes have the capacity to communicate the data they collect to another device, such as a control mechanism, or at minimum, be capable of storing the collected data for later retrieval. In some embodiments, such biosensors will be hard wired to controlling or other devices for communication of the data collected, e.g., the concentration of a pharmaceutical formulation in the fluids of the labyrinth (inner ear). In other embodiments, the biosensor will have a wireless connection (Wi-Fi/Bluetooth) to communicate these data to another device.

Figure 6:
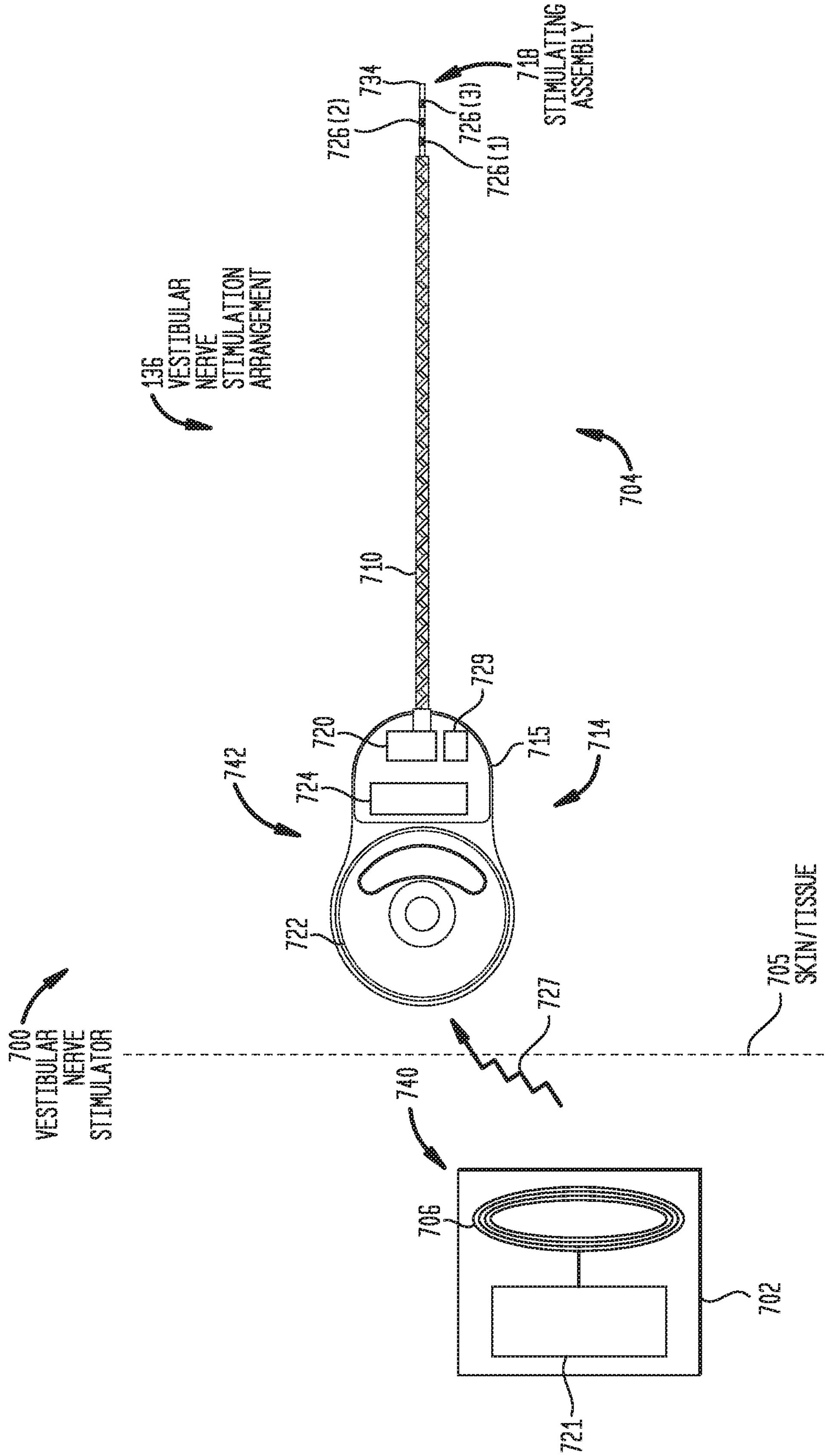
FIG. 6 schematically illustrates a vestibular nerve stimulator, according to aspects of the embodiments presented herein.

There are a number of different types of such partially or fully implantable medical devices with/in which embodiments presented herein may be implemented. For example, the techniques presented herein may be implemented with cochlear implants or other auditory prostheses, such as auditory brainstem stimulators, electro-acoustic hearing prostheses, direct cochlear stimulators, bimodal hearing prostheses, etc. The techniques presented herein may also be used with balance prostheses (e.g., vestibular implants), retinal or other visual prosthesis/stimulators, occipital cortex implants, sensor systems, cardiac devices (e.g., implantable pacemakers, defibrillators, etc.), drug delivery systems, catheters, seizure devices (e.g., devices for monitoring and/or treating epileptic events), sleep apnea devices, electroporation devices, spinal cord stimulators, deep brain stimulators, motor cortex stimulators, sacral nerve stimulators, pudendal nerve stimulators, vagus/vagal nerve stimulators, trigeminal nerve stimulators, diaphragm (phrenic) pacers, pain relief stimulators, other neural, neuromuscular, or functional stimulators, etc. FIG. 6 is a schematic diagram illustrating a balance prosthesis with which the techniques presented herein may be implemented.

More specifically, certain individuals may suffer from a balance disorder with complete or partial loss of vestibular system function/sensation in one or both ears. In general, a balance disorder is a condition in which an individual lacks the ability to control and/or maintain a proper (balanced) body position in a comfortable manner (i.e., the recipient experiences some sensation(s) of disbalance). Disbalance, sometimes referred to herein as balance problems, can manifest in a number of different manners, such as feelings of unsteadiness or dizziness, a feeling of movement, spinning, or floating, even though standing still or lying down, falling, difficulty walking in darkness without falling, blurred or unsteady vision, inability to stand or walk unaided, etc. Balance disorders can be caused by certain health conditions, medications, aging, infections, head injuries, problems in the inner ear, problems with brain or the heart, problems with blood circulation, etc. In general, a "balance prosthesis" or "balance implant" is a medical device that is configured to assist recipients (i.e., persons in which a balance prosthesis is implanted) that suffer from balance disorders.

As noted, FIG. 6 illustrates one example balance prosthesis, namely a vestibular nerve stimulator 700, in accordance with embodiments presented herein. More specifically, as shown in FIG. 6, the vestibular nerve stimulator 700 comprises an external component 702 and an implantable component 704, which is implantable within a recipient (i.e., implanted under the skin/tissue 705 of a recipient).

The external component 702 may comprise a number of functional and/or electronic elements used in the operation of the vestibular nerve stimulator 700. However, for ease of understanding, FIG. 6 only illustrates external radio frequency (RF) interface circuitry 721 and an external coil 706. The external coil 706 is part of an external resonant circuit 740. As described further below, the external RF interface circuitry 721 comprises data drive circuitry 744 and power drive circuitry 746 which are selectively activated/used for transcutaneous transmissions of data and power, respectively, to the implantable component 704.

The implantable component 704 comprises an implant body (main module) 714 and a vestibular stimulation arrangement 737. The implant body 734 generally comprises a hermetically-sealed housing 715 in which a number of functional and/or electronic elements used in the operation of the vestibular nerve stimulator 700 may be disposed. However, for ease of understanding, FIG. 6 only illustrates internal radio frequency (RF) interface circuitry 724, a stimulator unit 720, and a rechargeable battery 729. The implant body 734 also includes an internal/implantable coil 722 that is generally external to the housing 715, but which is connected to the internal RF interface circuitry 724 via a hermetic feedthrough (not shown in FIG. 6). The implantable coil 722 is part of an implantable resonant circuit 742. The stimulator unit 720 may include, for example, one or more current sources, switches, etc., that collectively operate to generate and deliver the electrical stimulation signals to the recipient via the vestibular stimulation arrangement 737.

As shown in FIG. 6, the vestibular stimulation arrangement 737 comprises a lead 716 and a vestibular nerve stimulating (electrode) assembly 718. The stimulating assembly 718 comprises a plurality of electrodes 726 (1), 726 (2) and 726 (3) disposed in a carrier member 734 (e.g., a flexible silicone body). In this specific example, the stimulating assembly 718 comprises three (3) electrode contacts (electrodes), referred to as electrode contacts 726 (1), 726(2), and 726(3). The electrode contacts 726(1), 726(2), and 726(3) function as an electrical interface to the recipient's vestibular nerve. It is to be appreciated that this specific embodiment with three electrodes is merely illustrative and that the techniques presented herein may be used with stimulating assemblies having different numbers of electrodes, stimulating assemblies having different lengths, etc.

The stimulating assembly 718 is configured such that a surgeon can implant the stimulating assembly, for example, adjacent the otolith organs of the peripheral vestibular system (e.g., via, the recipient's oval window). That is, the stimulating assembly 718 has sufficient stiffness and dynamics such that the stimulating assembly can be inserted through the oval window and placed reliably within the bony labyrinth adjacent the otolith organs (e.g., sufficient stiffness to insert the stimulating assembly to the desired depth between the bony labyrinth and the membranous labyrinth).

As noted above, the external component 702 comprises an external resonant circuit 740, which includes the external coil 706. Similarly, the implantable component 704 comprises an implantable resonant circuit 742, which includes the implantable coil 722. When the coils 706 and 722 are positioned in close proximity to one another, the coils form a transcutaneous closely-coupled wireless link 727. This closely-coupled wireless link 727 formed between the external coil 706 with the implantable coil 722 may be used to transfer power and/or data from the external component 702 to the implantable component 704. That is, the external RF interface circuitry 721 is configured to drive (energize) the external coil 706 in a manner that sends power and/or data to the implantable component 704.

In the example of FIG. 6, the vestibular nerve stimulator 700 is configured to generate a localized activation field within the body of the recipient. More specifically, the vestibular nerve stimulator 700 is implanted in or adjacent to the vestibular system of the recipient and is configured to deliver electrical stimulation (current) signals to the vestibular system (e.g., peripheral vestibular system, otolith organs, vestibular nerve, etc.) of the recipient. That is, the vestibular nerve stimulator 700 sources (delivers) current to the recipient via one or more implanted electrode contacts 726(1)-726(3) or another electrode (not shown), while also sinking the current via a different one or more of the implanted electrode contacts 726(1)-726(3) or another electrode. The flow of current generated by the vestibular nerve stimulator 700 induces a localized electromagnetic field (EMF) within the immediate vicinity/proximity of vestibular nerve stimulator.

Figure 7:
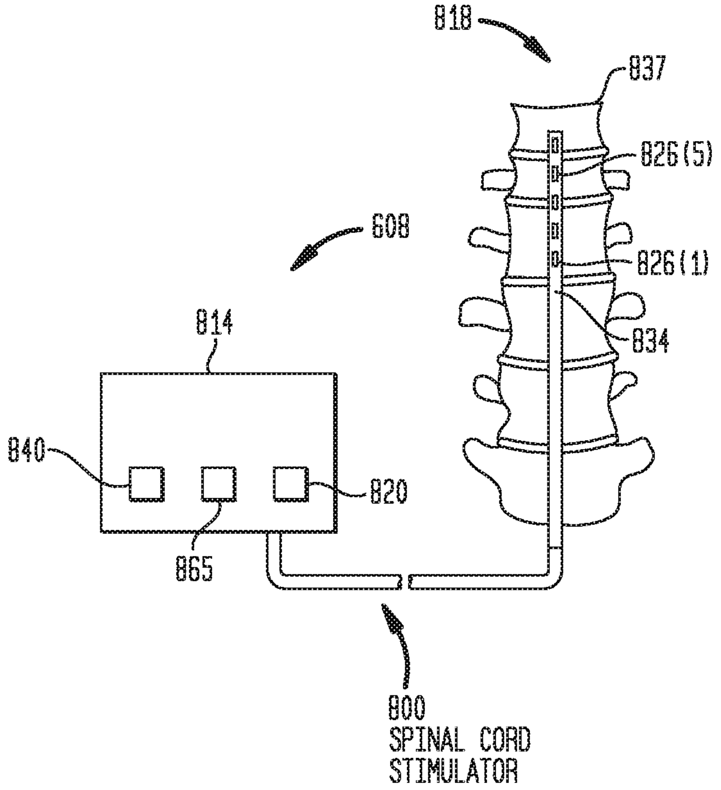
FIG. 7 is a schematic diagram illustrating a balance prosthesis with which certain embodiments presented herein may be implemented.
Figure 8:
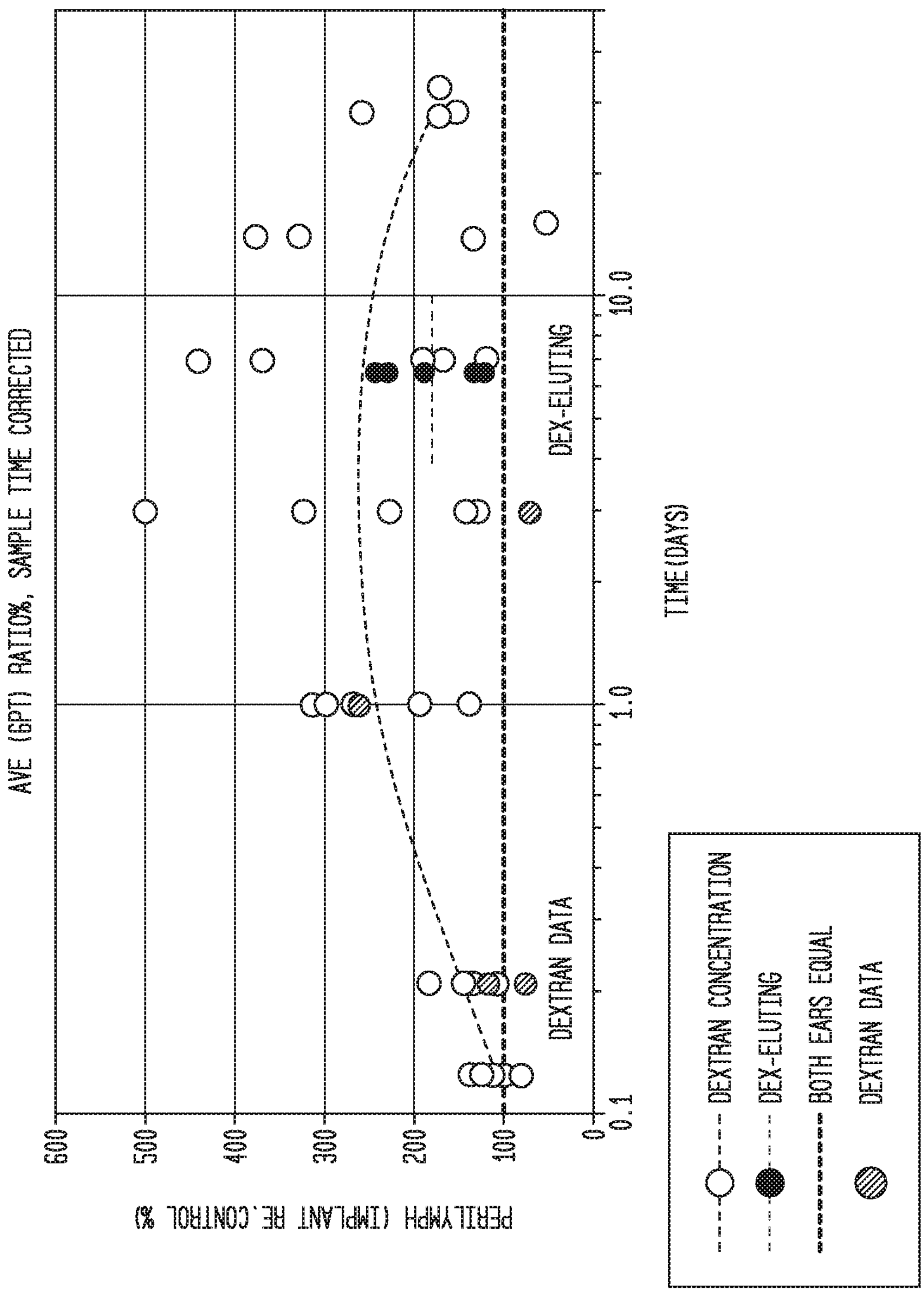
FIG. 8 shows experimental data of dextran concentration as a function of time after implantation, according to aspects of the embodiments presented herein. As an example, dextran was administered through a cannula in the jugular vein by continuous IV injection.

In another example, a recipient of a spinal cord stimulator could regularly (e.g., daily) orally ingest a pharmaceutical formulation (as a therapeutic substance). FIG. 7 is a simplified schematic diagram illustrating an example spinal cord stimulator 800 that maybe used in one such implementation, in accordance with embodiments presented herein.

The spinal cord stimulator 800 includes a main implantable component (implant body) 814, and a stimulating assembly 818, all implanted in a recipient. The main implantable component 814 comprises a wireless transceiver 840, a battery 865, and a stimulator unit 875. The stimulator unit 875 comprising, among other elements, one or more current sources on an integrated circuit (IC).

The stimulating assembly 818 is implanted in a recipient adjacent/proximate to the recipient's spinal cord 837 and comprises five (5) stimulation electrodes 826, referred to as stimulation electrodes 826(1)-826(5). The stimulation electrodes 826(1)-826(5) are disposed in an electrically insulating carrier member 834 and are electrically connected to the stimulator 820 via conductors (not shown) that extend through the carrier member 834.

Following implantation, the stimulator unit 820 is configured generate stimulation signals for delivery to the spinal cord 837 via stimulation electrodes 826(1)-826(5). Although not shown in FIG. 7, an external controller may also be provided to transmit signals through the recipient's skin/tissue to the stimulator unit 820 for control of the stimulation signals.

In the example of FIG. 7, the spinal cord stimulator 800 is configured to generate a localized activation field within the body of the recipient. More specifically, spinal cord stimulator 800 is implanted in or adjacent to the spinal cord 837 of the recipient and is configured to deliver electrical stimulation (current) signals to the spinal cord. That is, the spinal cord stimulator 800 700 sources (delivers) current to the recipient via one or more implanted electrode contacts 826(1)-826(5) or another electrode (not shown), while also sinking the current via a different one or more of the implanted electrode contacts 826(1)-826(5) or another electrode. The flow of current generated by the spinal cord stimulator 800 induces a localized electromagnetic field (EMF) within the immediate vicinity/proximity of spinal cord stimulator (i.e., the spinal cord 837).

Some embodiments may be made available as kits for modulating the BLB.

The disclosed embodiments described and claimed are not to be limited in scope by the specific preferred embodiments referenced herein, since these embodiments are intended as illustrations, not limitations. Any equivalent embodiments are intended to be within the scope of this disclosure, and the embodiments disclosed are not mutually exclusive. Indeed, various modifications to the embodiments, in addition to those shown and described herein will become apparent to those skilled in the art from the foregoing description. Such modifications are also intended to fall within the scope of the appended claims.

The terms and words used in the following description and claims are not limited to conventional definitions but, rather, are used to enable a clear and consistent understanding of the disclosure. Accordingly, it should be apparent to those skilled in the art that the description of various embodiments is provided for illustration purpose only and not for the purpose of limiting the disclosure with respect to the appended claims and their equivalents.

It is to be understood that the singular forms "a," "an," and "the" include the plural forms unless the context clearly dictates otherwise, e.g., reference to "a dermatologically active compound" includes reference to one or more such compounds.

Unless otherwise defined herein, all terms used have the same meaning as commonly understood by a person of ordinary skill in the art. Terms used herein should be interpreted as having meanings consistent with their meanings in the context of the relevant art.

As used herein, the terms "comprising," "comprise" or "comprised," in reference to defined or described elements of any item, composition, formulation, apparatus, method, process, system, etc., are intended to be inclusive or open ended, and includes those specified elements or their equivalents. Other elements can be included and still fall within the scope or definition of the defined item, composition, etc.

The term "about" or "approximately" means within an acceptable error range for the particular value as viewed by one of ordinary skill in the art; this depends in part on how the value is measured or determined based on the limitations of the measurement system.

"Co-administer" refers to the simultaneous administration of two pharmaceutical formulations in the blood or other fluid of an individual using the same or different modes of administration. Pharmaceutical formulations can be concurrently or sequentially administered in the same pharmaceutical carrier or in different ones.

The term "treatment" includes interventions such as monitoring, administering pharmaceutical formulation with the intent to modulate, alter or halt the pathology or symptoms of the condition, disorder or disease; and it further includes palliative and preventive care.

The verb "modulate" generally refers to changing, increasing, enhancing, promoting, decreasing, reducing, suppressing, blocking or acting as either an antagonist or agonist. The terms "subject," "patient," and "individual" are used interchangeably.

Example 1: Time Course of BLB Compromise Following Cochlear Implantation

When a cochlear device is surgically implanted with an electrode extending into the labyrinth of the inner ear, the BLB is disrupted, and its properties are altered. A result, the BLB becomes more permeable. Whether the increased permeability results from the immediate disruption of the BLB is unknown.

In some embodiments, methods for assessing a more permeable than normal blood labyrinth barrier (but not treating it or preventing it from becoming more permeable) involve injecting a pharmaceutical formulation functioning as a marker into the blood stream of a recipient, measuring the amount of formulation in the perilymph as a function of time. As the barrier becomes more permeable after implantation, the formulation may be detected in greater quantities in the perilymph. In this type of experiment, the data may be normalized to the contralateral ear (without an implant), which allows data to be collected from a single subject serving as its own "control."

We measured the time course of BLB compromise following cochlear implantation in guinea pigs to characterize the development of increasing BLB permeability relating to the BLB disruption that surgical implantation causes.

Figure 9:
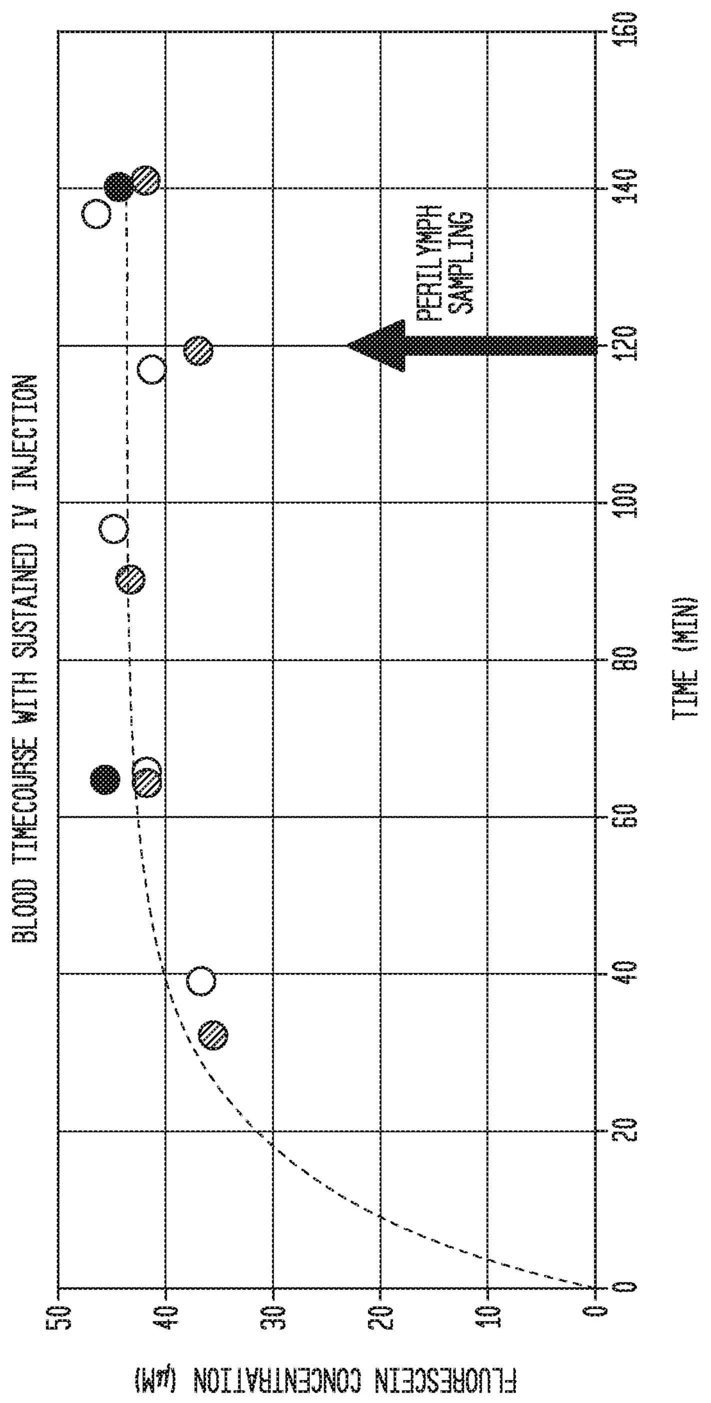
FIG. 9 shows the blood sampling time course with sustained IV injection at a rate of 20 μL/min of fluorescein (20 mM), with data points (as represented in the legend of FIG. 8) fit to the dotted line.
Figure 10:
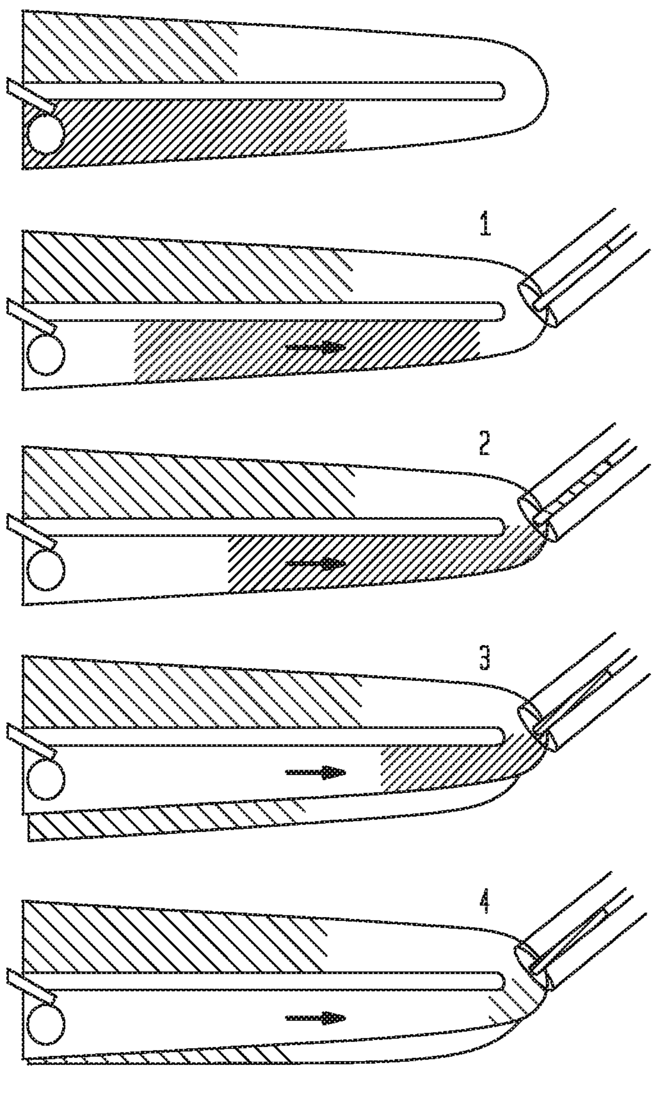
FIG. 10 shows sequential perilymph sampling from the cochlear apex to provide an index of the distribution of a marker administered intravenously. The cochlear apex was prepared for fluid sampling by building a hydrophobic cup of silicone adhesive around it. When the apex is perforated the emerging fluid (area with hatch marks below and moving to the right) collects in the cup without any loss to the middle ear. Ten samples were collected sequentially using separate capillary tubes, as shown. The perilymph is pushed to the right by cerebral spinal fluid entering the scala tympani (ST) on the left in the basal turn. Sample 1 contains perilymph originating near the cochlear apex, while later samples, 2-4, originate from more basal locations, providing an index of the distribution of the marker along the ST.
Figure 11A:
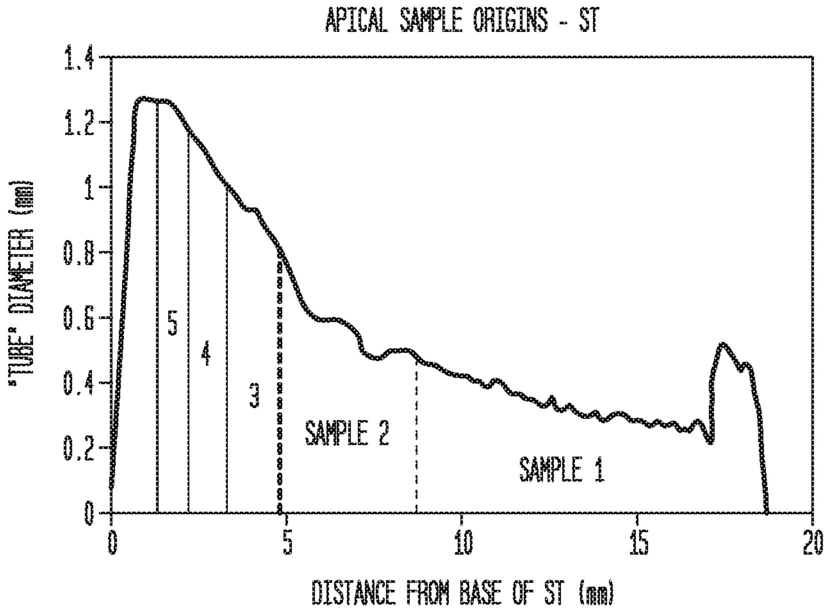
FIGS. 11A and 11B show the calculated origins of the first five perilymph samples along the ST without (FIG. 11A) and with (FIG. 11B) a cochlear implant in place, which has only a small influence on the later drawn samples.
Figure 11B:
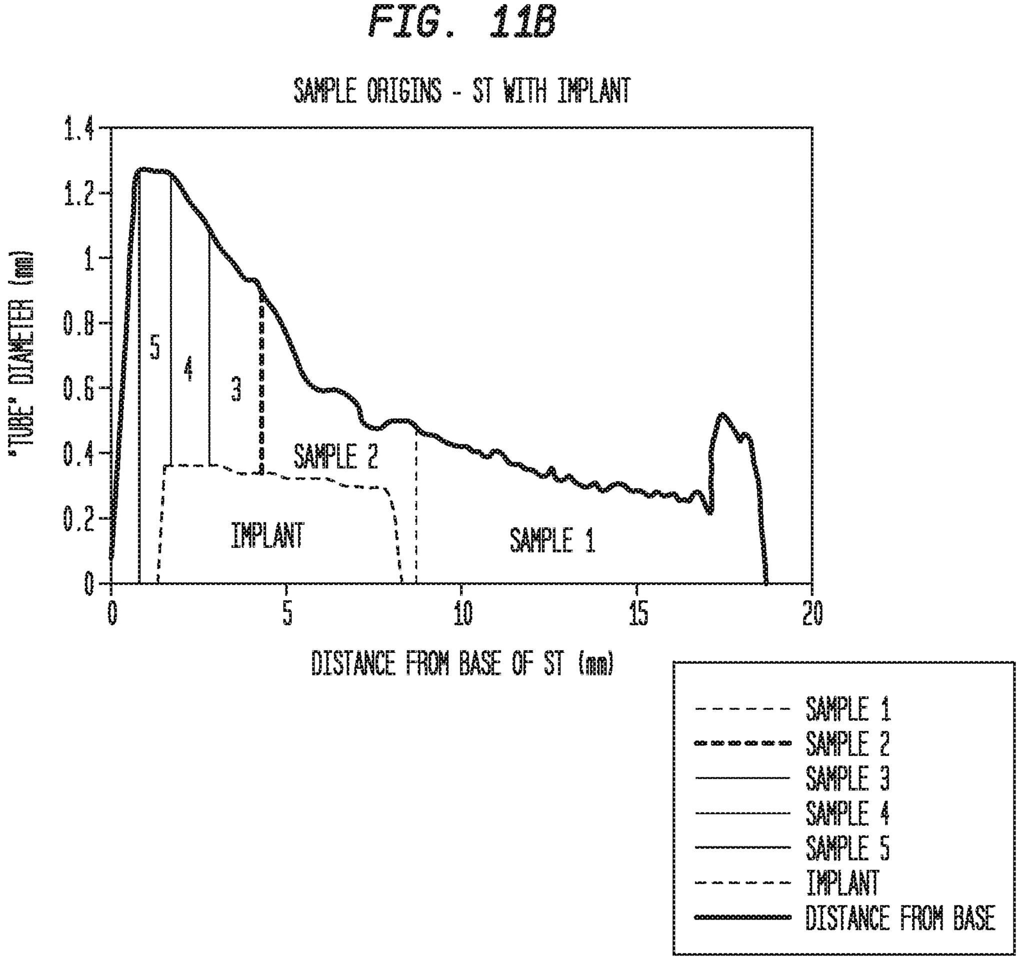

Fluorescein (20 mM) was administered through a cannula in the jugular vein by continuous intravenous (IV) injection at a rate of 20 μL/minute. FIG. 9 shows the calculated time course with sustained IV infusion into a 183 mL volume with elimination half time of 11 minutes; we used these data for computer simulations described below. Implants were placed through a cochleostomy into the basal turn of the scala tympani. Perilymph sampling began two hours after IV infusion began, and the concentration of fluorescein in the perilymph was used as a proxy for BLB permeability. Sampling in the perilymph was accomplished as follows: The cochlear apex was prepared for fluid sampling by building a hydrophobic cup of silicone adhesive around it. When the apex was perforated, the emerging fluid collected in the cup without loss into the middle ear. Ten samples were collected in sequence, with each taking 60 to 90 seconds. Fluid was collected into separate capillary tubes as shown in FIG. 10, where perilymph (darker, hatched region below) was pushed to the right by cerebral spinal fluid entering the scala tympani (ST) on the left in the basal turn. Sample 1 shown in FIG. 10 contains perilymph originating near the cochlear apex, while samples 2-4 originate from more basal locations, providing an index of the distribution of the marker along the ST. Fluorescein concentrations were compared for implanted versus non-implanted years, and from ears of non-implanted control animals. FIG. 11 shows the calculated origins of the first five perilymph samples along the ST without (a) and with (b) a cochlear implant in place, which has only a small influence on the later drawn samples.

Figure 12:
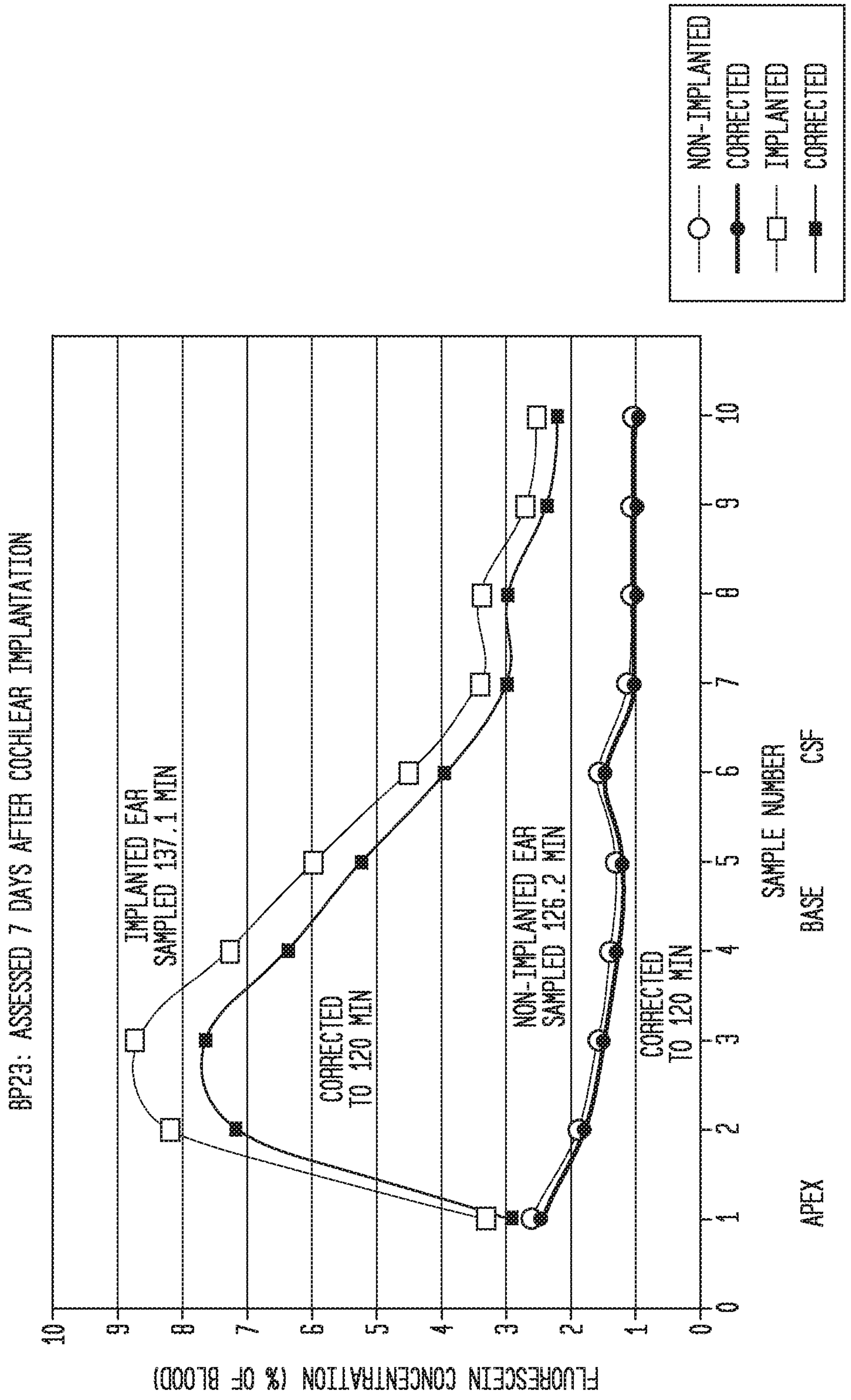
FIG. 12 shows plasma fluorescein concentration in perilymph as a percent of its plasma concentration in implanted ears top set of lines (with correction) versus non-implanted ears bottom set of lines (with correction) for each of the ten samples. Seven days following cochlear implantation, the perilymph was sampled at 126 minutes (non-implanted, large open circles) and 127 minutes (implanted large, open squares) after the start of IV fluorescein infusion began (shown in solid symbols). Smaller, filled in circles and squares represent the same data corrected to a sample time beginning at 120 minutes after the start of the infusion, assuming a linear rate of entry through the BLB over time.
Figure 13:
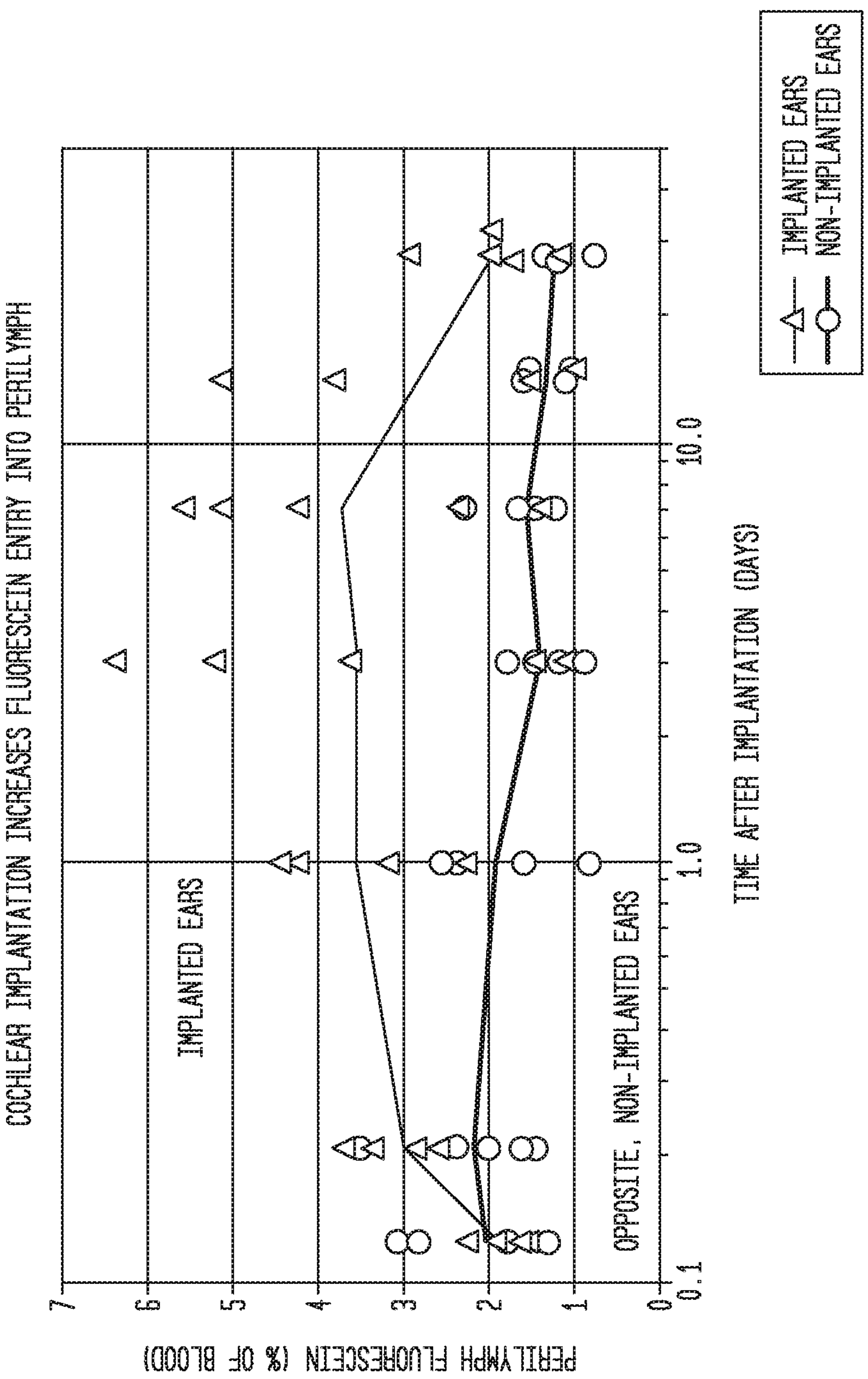
FIG. 13 shows the concentration of fluorescein in perilymph as a percent of its concentration in plasma in non-implanted ears (control, circle markers) versus from implanted ears (triangle markers) for each animal sampled at seven time points: immediately at implantation, at 5 hours, 1, 3, 7, 14 and 28 days after implantation with an 8-electrode array. The use of an 8-electrode array is merely illustrative and other types of electrodes, for example with different numbers of electrodes, could be used in alternative arrangements.

FIG. 12 shows plasma fluorescein concentration in perilymph as a percent of its plasma concentration in implanted ears (upper set of data series) versus non-implanted ears (lower set of data series) for each of the ten samples. Seven days following cochlear implantation, the perilymph was sampled at 126 minutes (non-implanted) and 127 minutes (implanted) after the start of IV fluorescein infusion began (shown in solid symbols). Open symbols show the same data corrected to a sample time beginning at 120 minutes after the start of the infusion, assuming a linear rate of entry through the BLB over time. FIG. 13 shows the concentration of fluorescein in perilymph as a percent of its concentration in plasma in non-implanted ears (non-implanted, open circle markers) versus from implanted ears (open triangle markers) for each animal sampled at seven time points: immediately at implantation, at 5 hours, 1, 3, 7, 14 and 28 days after implantation with an HL-8 electrode. Each sample time represents the mean of samples 1-6 from one ear; lines represent the group (n=5) mean. Early after implantation, entry of fluorescein, representing the permeability of the BLB, for both ears is similar, indicating that entry of the fluorescein into the perilymph does not result from "insertion trauma."

Figure 14:
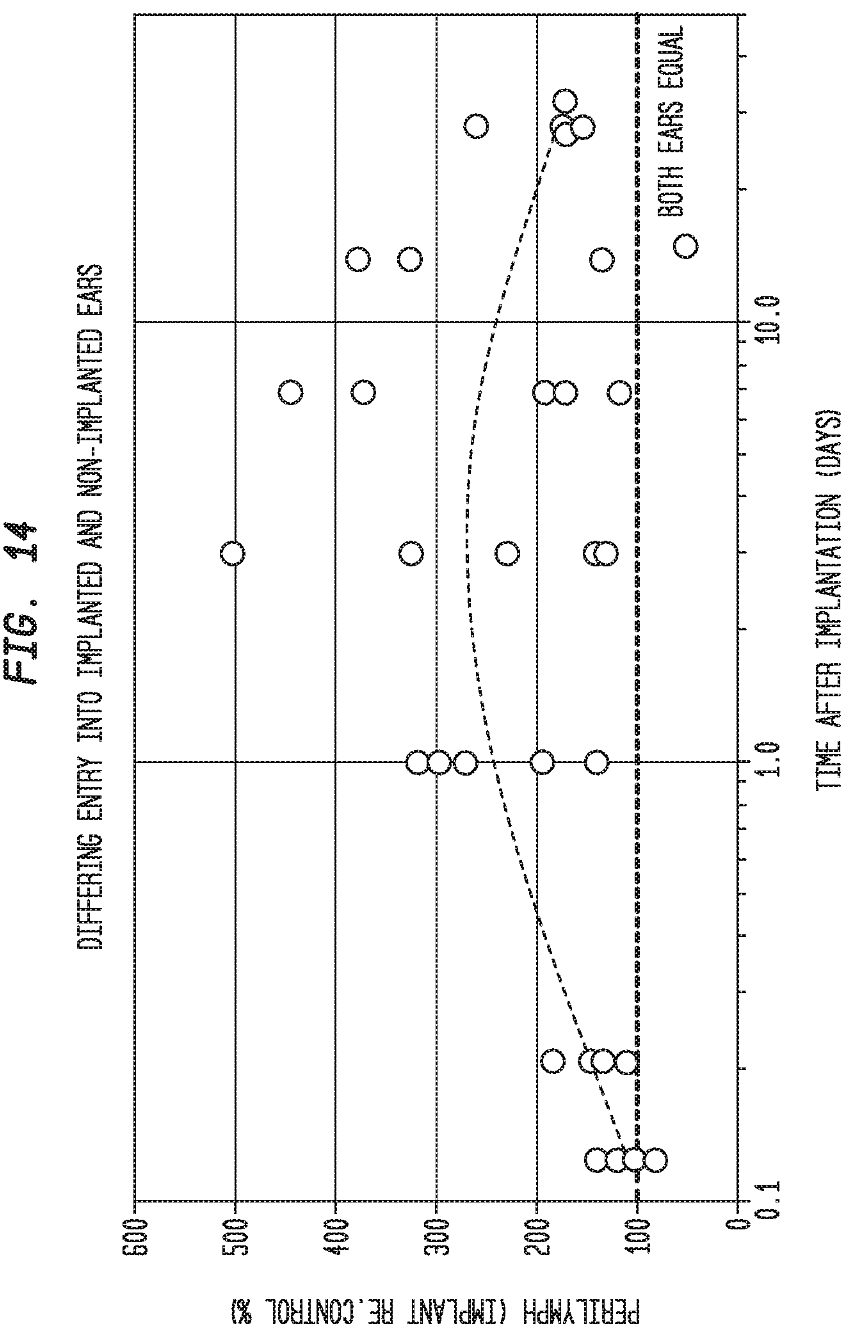
FIG. 14 shows fluorescein concentration of the implanted ear expressed as a percentage of that in the non-implanted ear in the same animal, and the time course of increased permeability for each animal (open circle markers). The increase in permeability develops progressively during the first day after implantation and peaks around three to seven days after implantation. By 14 and 28 days, BLB permeability is reduced closer to pre-implant levels. On average, BLB permeability increased two- to three-fold in the implanted versus nonimplanted ear.

FIG. 14 shows fluorescein concentration of the implanted ear expressed as a percentage of that in the non-implanted ear in the same animal, and the time course of increased permeability for each animal (open circle markers). The increase in permeability develops progressively during the first day after implantation and peaks around three to seven days after implantation. By 14 and 28 days, BLB permeability is reduced closer to pre-implant levels. On average, BLB permeability increased two- to three-fold in the implanted versus nonimplanted ear.

Figure 15:
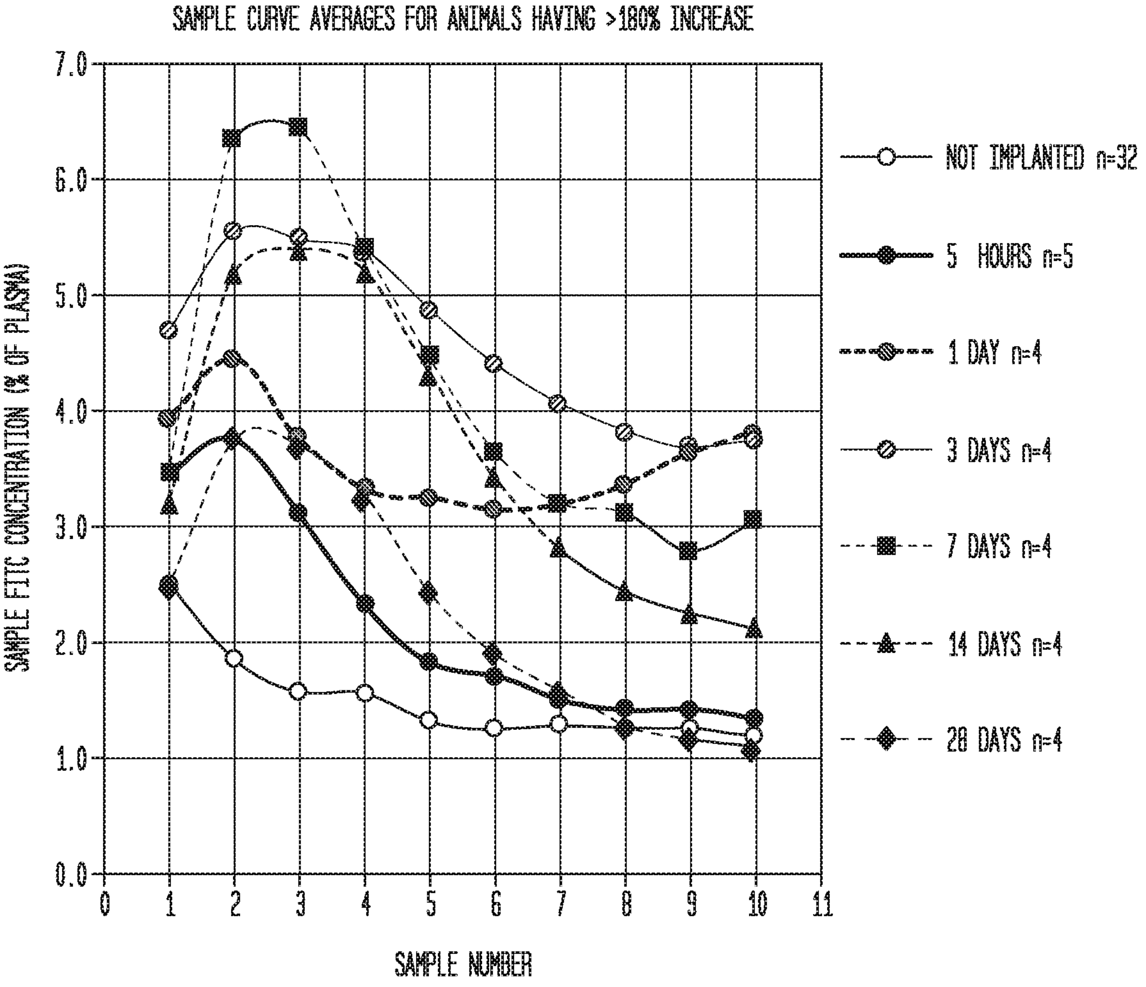
FIG. 15 shows the group mean original sampling curves consisting of ten sequential samples for each of the animals in each sampling time group, as indicated. These data are for select subsets of animals that exhibited increased implant-induced fluorescein entry (permeability), to a degree exceeding 180% of that of the non-implanted ear. Curve shape provides a good indication of the location along the ST where permeability is increased, and fluorescein entered. For early sampling times (5 hrs., 1 day) the highest fluorescein concentration is present in sample 2. Later, samples 3 and 4 are relatively higher, which corresponds to entry of fluorescein into more basal regions of the cochlea.

FIG. 15 shows the group mean original sampling curves consisting of ten sequential samples for each of the animals in each sampling time group, as indicated. These data are for select subsets of animals that exhibited increased implant-induced fluorescein entry (permeability), to a degree exceeding 180% of that of the non-implanted ear. Curve shape provides a good indication of the location along the ST where permeability increased, and fluorescein entered. For early sampling times (5 hours, 1 day) the highest fluorescein concentration is present in sample 2. Later, samples 3 and 4 are relatively higher, which corresponds to entry of fluorescein into more basal regions of the cochlea.

Figure 16A:
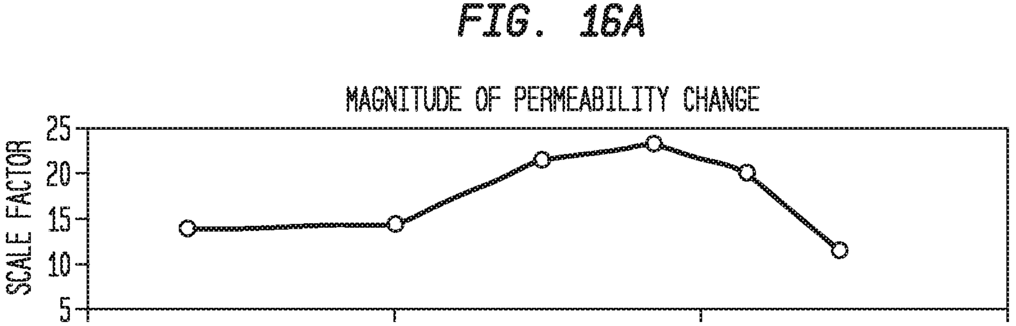
FIGS. 16A, 16B, and 16C show results generated from computer simulations of the data, including the magnitude (FIG. 16A) and spatial localization (FIG. 16B, hatched region) of the BLB permeability increase. Initially the increase coincides with the implant location (FIG. 16C) lower left). Over time, increasing permeability occurs at more basal regions of the cochlea and dominates the result.
Figure 16B:
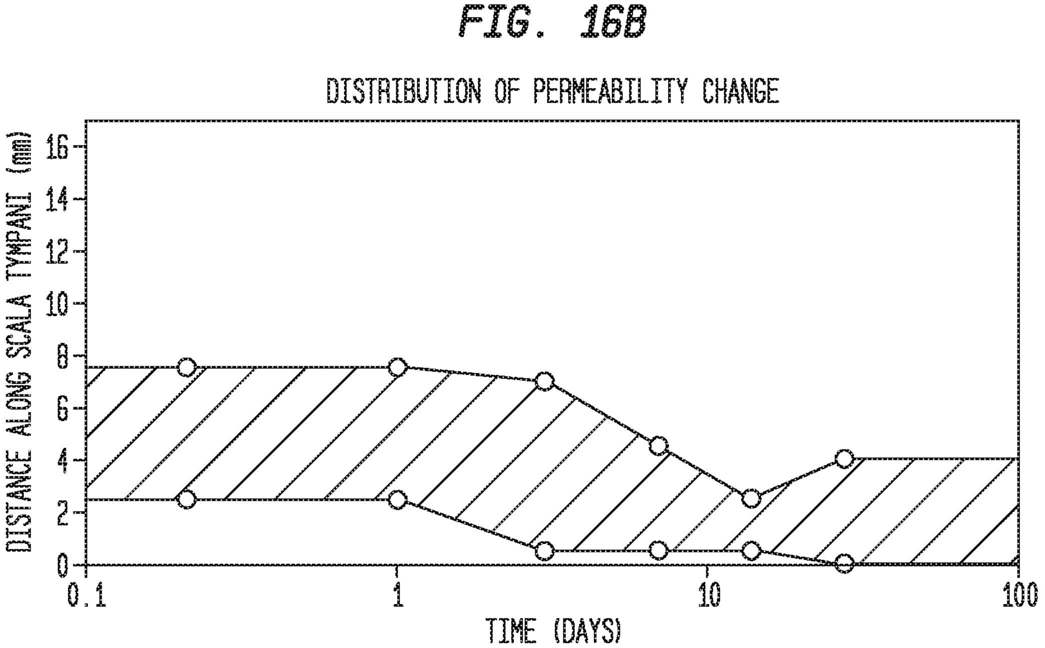
Figure 16C:
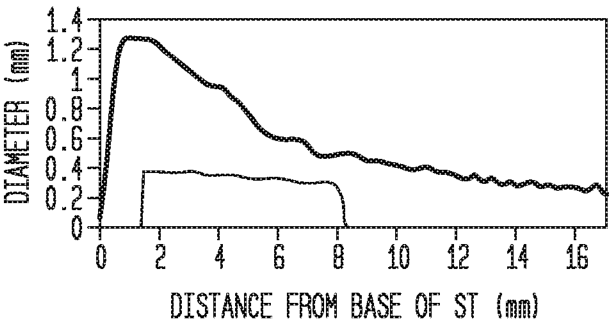
Figure 17:
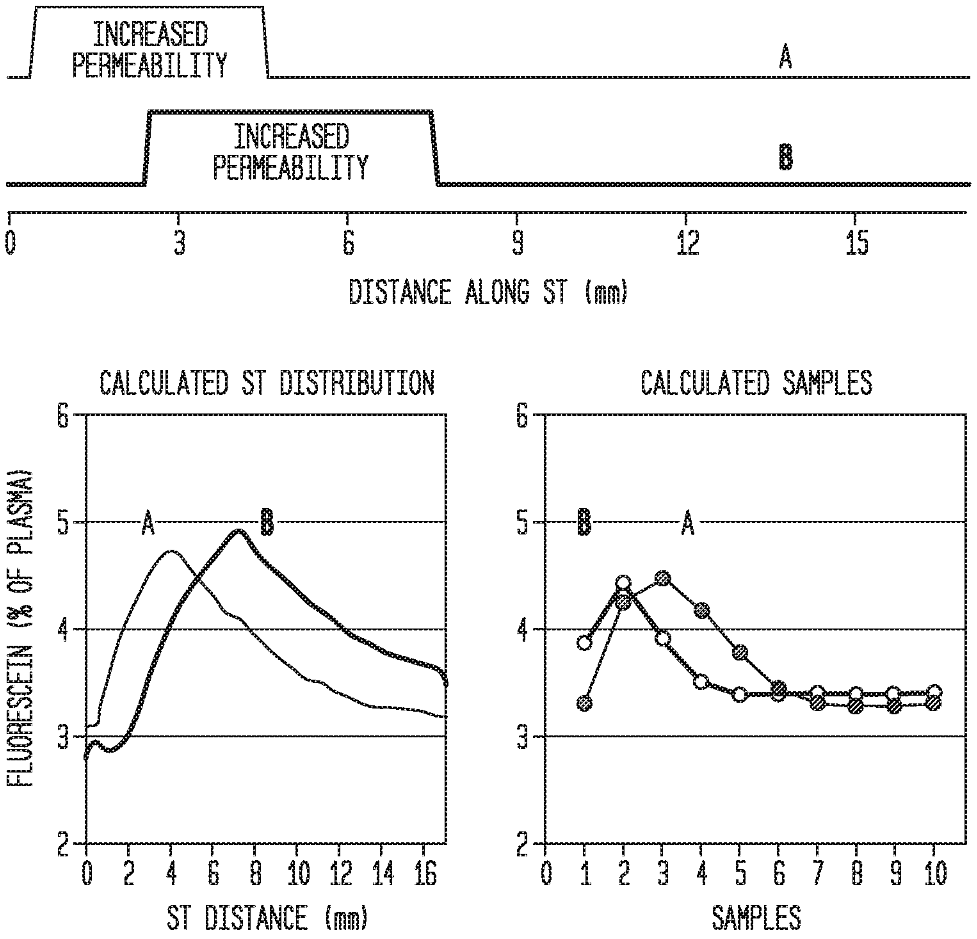
FIG. 17 also shows the results of computer simulations using data collected in this experiment. The simulation results indicate that the shapes of sequential sample curves depend on the location of the permeability increase in the ST. Distribution and sample curves are calculated for a basal region of increased permeability (line A, thinner line, filled in circle markers) and for a more apical region of increased permeability (line B, thicker line, open circle markers).
Figure 18:
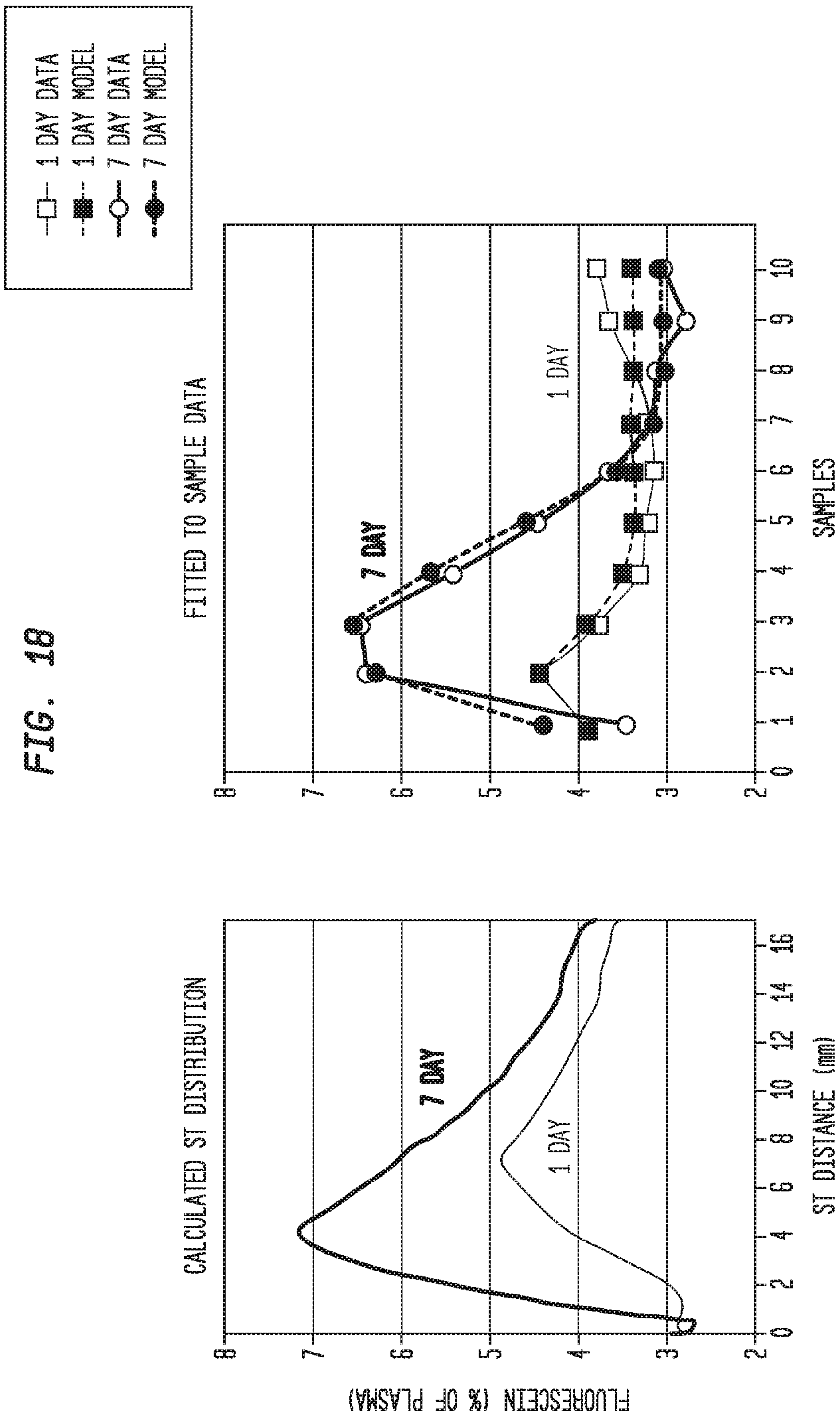
FIG. 18 shows further results of computer simulations fitted to day 1 and day 7 sample data. One day after implantation, the BLB permeability increase was consistent with permeability of distribution type B (in FIG. 17), while at day 7, the increase was consistent with a permeability distribution of type A.

We also used the data collected to perform computer simulations (FIGS. 16-18) to analyze spatial localization and magnitude of BLB permeability. FIG. 16 shows results derived from computer simulations of the data, including the magnitude ((a) top right) and spatial localization ((b) bottom right, hatched region) of the BLB permeability increase. Initially the increase coincides with the implant location ((c) lower left). Over time, increasing permeability occurs at more basal regions of the cochlea and dominates the result. The figure on the lower left (c) depicts the location of the implant relative to the scala tympani (ST), and informs the data shown in (b). FIG. 17 also shows the results of computer simulations using data collected in this experiment. The simulation results indicate that the shapes of sequential sample curves depend on the location of the permeability increase in the ST. Distribution and sample curves are calculated for a basal region of increased permeability (A, hatched circle markers) and for a more apical region of increased permeability (B, open circle markers with thicker line). FIG. 18 shows further results of computer simulations fitted to day 1 and day 7 sample data. One day after implantation, the BLB permeability increase was consistent with permeability of distribution type B (in FIG. 17), while at day 7, the increase was consistent with a permeability distribution of type A.

Figure 19:
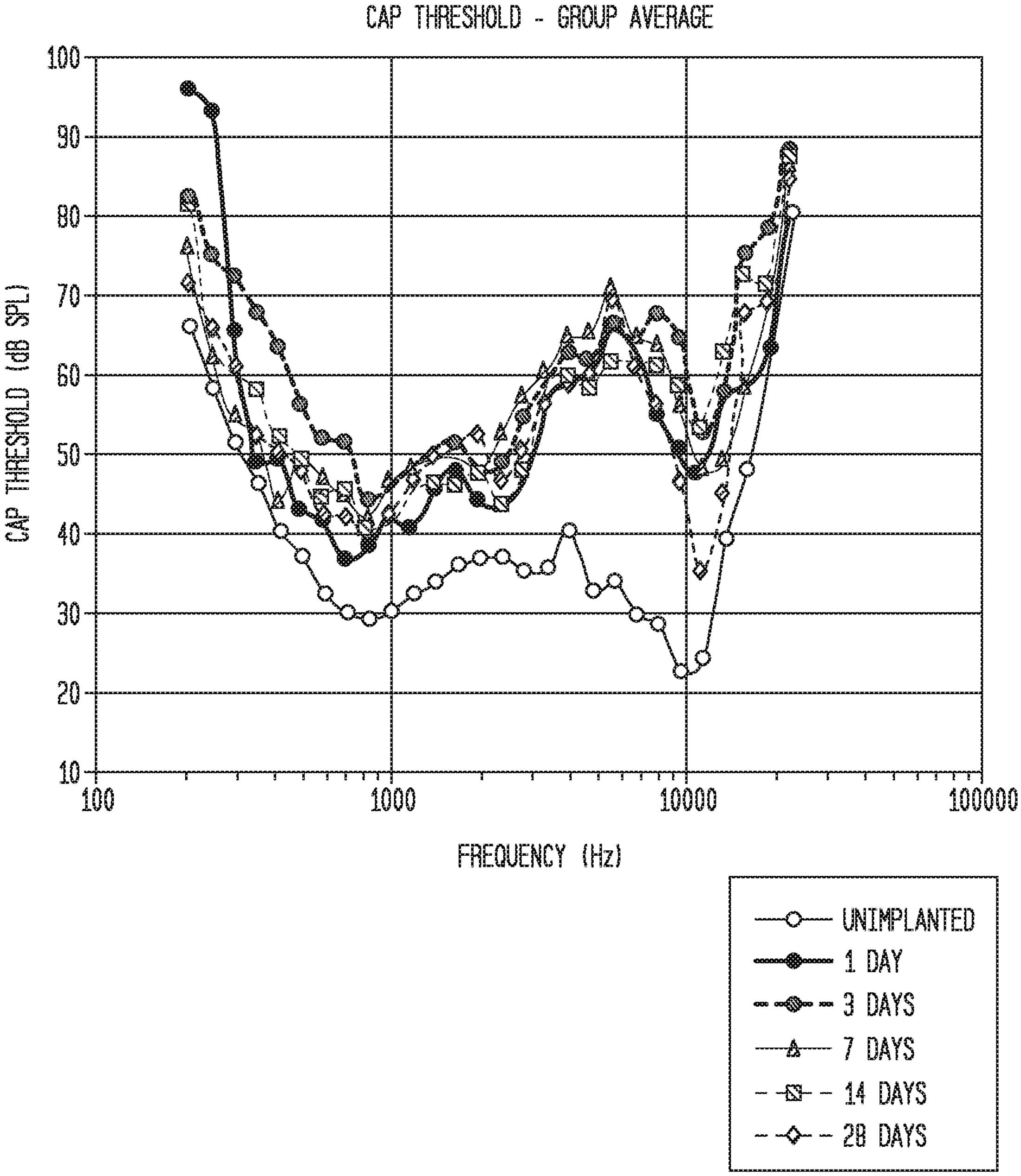
FIG. 19 shows the group mean cochlear action potential (CAP) threshold curves for non-implanted (open circle marker and solid line) and implanted ears (all other markers and line types). Thresholds of all implanted groups were relatively similar, with maximum threshold elevation in the 4-8 kHz region.
Figure 20:
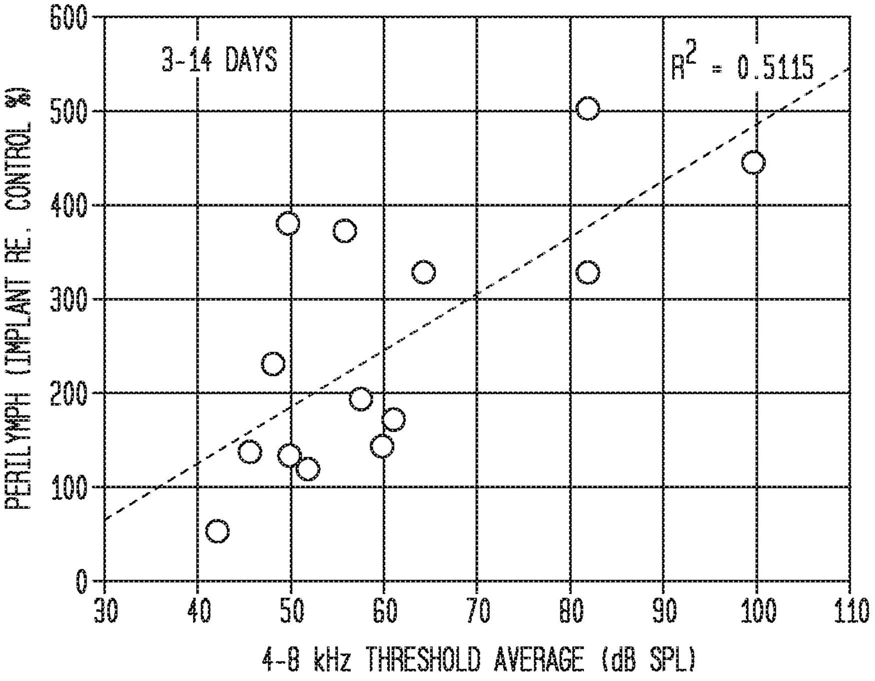
FIG. 20 shows the correlation ($p<0.05$) from 3-14 days between measured BLB permeability increase and hearing loss. Hearing sensitivity mean across the 4-8 kHz measurements was modestly correlated with BLB permeability in all groups between 3-14 days post implantation.

We further looked at the cochlear action potential threshold curves. FIG. 19 shows the group mean cochlear action potential (CAP) threshold curves for non-implanted (open circle markers and solid line) and implanted ears (all other markers and line types). Thresholds of all implanted groups were relatively similar, with maximum threshold elevation in the 4-8 kHz region. Finally, we looked at the correlations at different time periods between the BLB permeability and hearing thresholds; we found a modest correlation from 3-14 days in all groups (FIG. 20).

In sum, we used a sampling method that enabled us to demonstrate variations along the scala tympani. Permeability of the BLB initially appeared to be localized to the region of the implant but over time transitioned to be greater at a more basal location, perhaps at the level of the cochleostomy. Importantly, we found that although insertion trauma disrupted the BLB to an extent, it did not lead to significant impairment of the BLB in the early hours following implantation but, rather, permeability developed slowly over a few days, suggesting a role in increased permeability through an immune response. Permeability returned toward a pre-implantation level by about 28 days post-implantation.

We note that hearing loss from CI implantation apparently can arise from multiple sources such as direct mechanical and/or electrochemical influences of the implant; insertion trauma or from immune responses and increasing permeability of the BLB. In this study we found a correlation between elevated permeability levels and elevated thresholds, supporting the view that the degree of inflammatory response (and BLB permeability) may contribute to residual hearing loss. Changes in the BLB properties after cochlear implantation may play a role in drug pharmacokinetics and contribute to post-operative physiological changes affecting outcomes such as residual hearing.

What is claimed is:

1. A medical device comprising:

a sensor configured to be implanted in a recipient of the medical device and to obtain measurements from an inner ear of the recipient; and a processor configured to:

detect changes in a permeability of a blood labyrinth barrier of the inner ear based on the measurements obtained by the sensor; and adjust operation of the medical device based on the changes in the permeability of the blood labyrinth barrier.

2. The medical device of claim 1, wherein the sensor is configured to detect at least one type of inflammatory cytokine within the inner ear of the recipient.

3. The medical device of claim 2, wherein the processor is configured to detect the changes in the permeability of the blood labyrinth barrier based on a change in a concentration of at least one type of inflammatory cytokine selected from the group consisting essentially of tumor necrosis factor-α (TNF-α), interleukin-1β (IL-1β), and interleukin-6 (IL-6).

4. The medical device of claim 2, wherein the processor is configured to estimate the permeability of the blood labyrinth barrier based on changes in a concentration of the at least one type of inflammatory cytokine.

5. The medical device of claim 1, wherein the processor is configured to initiate one or more restorative actions that reduce the permeability of the blood labyrinth barrier.

6. The medical device of claim 1, wherein the sensor is configured to be implanted at least partially within the inner ear of the recipient and contact fluids of perilymph compartments or endolymph compartments of the inner ear of the recipient.

7. The medical device of claim 1, wherein the processor is configured to compare the permeability of the blood labyrinth barrier to a baseline permeability of the blood labyrinth barrier, and determine a hearing loss of the recipient based on comparison of the permeability of the blood labyrinth barrier to the baseline permeability of the blood labyrinth barrier.

8. The medical device of claim 7, wherein the medical device comprises a cochlear implant.

9. A method comprising:

obtaining one or more measurements from an inner ear of a recipient of a medical device;

determining, based on the one or more measurements, an increased permeability of a blood labyrinth barrier of the inner ear; and based on the determining, at least one of administering a pharmaceutical formulation or editing genes to reduce permeability of the blood labyrinth barrier.

10. The method of claim 9, wherein the one or more measurements indicate a concentration of cytokine in the inner ear of the recipient.

11. The method of claim 9, wherein the pharmaceutical formulation inhibits cytokine expression or activity.

12. The method of claim 9, wherein the pharmaceutical formulation comprises a corticosteroid, a compound with anti-pneumolysin activity, a compound with anti-caveolin-1 activity, or any combination thereof.

13. The method of claim 9, wherein the pharmaceutical formulation comprises a small interfering ribonucleic acid to interfere with production of connexin 43.

14. The method of claim 9, wherein editing the genes comprises excising or replacing a section of the genes associated with encoding regulators or cytokine availability at the blood labyrinth barrier.

15. A method comprising:

an implantable medical device obtaining measurements from an inner ear of a recipient of the implantable medical device over a period of time following implantation of the implantable medical device;

detecting, based on the measurements obtained by the implantable medical device, changes to a permeability of a blood labyrinth barrier of the recipient; and adjusting operation of the implantable medical device in response to the changes to the permeability of the blood labyrinth barrier.

16. The method of claim 15, wherein the method comprises detecting at least one type of inflammatory cytokine within the inner ear of the recipient.

17. The method of claim 15, wherein the method comprises detecting the changes in the permeability of the blood labyrinth barrier based on a change in a concentration of at least one type of inflammatory cytokine selected from the group consisting essentially of tumor necrosis factor-α (TNF-α), interleukin-1β (IL-1β), and interleukin-6 (IL-6).

18. The method of claim 15, wherein the method comprises initiating one or more restorative actions that reduce the permeability of the blood labyrinth barrier.

19. The method of claim 15, wherein adjusting the operation of the implantable medical device comprises delivering a pharmaceutical formation via the implantable medical device.

20. The method of claim 15, wherein the implantable medical device comprises a neurostimulator, and adjusting the operation of the neurostimulator comprises adjusting electrical stimulation provided by the neurostimulator to induce a hearing percept based on hearing loss indicated by the changes to the permeability of the blood labyrinth barrier.

* * * * *